(12) United States Patent
Black et al.

(10) Patent No.: US 11,801,144 B2
(45) Date of Patent: Oct. 31, 2023

(54) METHODS OF MAKING MEDICAL DEVICES

(71) Applicant: DeGen Medical, Inc., Florence, SC (US)

(72) Inventors: Craig Black, Florence, SC (US); Kyle Atwood, Darlington, SC (US); Charles Baskin, Florence, SC (US)

(73) Assignee: DeGen Medical, Inc., Florence, SC (US)

( * ) Notice: Subject to any disclaimer, the term of this patent is extended or adjusted under 35 U.S.C. 154(b) by 1425 days.

(21) Appl. No.: 16/130,744

(22) Filed: Sep. 13, 2018

(65) Prior Publication Data

US 2019/0076258 A1   Mar. 14, 2019

Related U.S. Application Data

(60) Provisional application No. 62/558,492, filed on Sep. 14, 2017.

(51) Int. Cl.
*A61F 2/30* (2006.01)
*B33Y 40/20* (2020.01)
(Continued)

(52) U.S. Cl.
CPC .......... *A61F 2/30942* (2013.01); *A61F 2/442* (2013.01); *B24B 1/00* (2013.01);
(Continued)

(58) Field of Classification Search
CPC .................................................. A61F 2/30942
See application file for complete search history.

(56) References Cited

U.S. PATENT DOCUMENTS 5,307,594 A * 5/1994 Panchison ................. B24C 1/04
                                                                    451/29
5,653,763 A    8/1997 Errico et al.
(Continued)

FOREIGN PATENT DOCUMENTS

| CN | 101460117 | 6/2007 |
| CN | 101049254 | 5/2010 |

(Continued)

OTHER PUBLICATIONS

European Patent Office, Extended European Search Report for Application No. 15162843.5, Jul. 5, 2016, p. 1-6.
(Continued)

*Primary Examiner* — Sarang Afzali
(74) *Attorney, Agent, or Firm* — MacMillan, Sobanski & Todd, LLC

(57) ABSTRACT

Methods of making medical devices are described. An example device is an implant used in spaces between vertebrae in a vertebral column of an animal. The example medical device includes a main body that has a lengthwise axis, a proximal end, a distal end, a length that extends from the proximal end to the distal end, an upper wall, a lower wall, a first lateral wall, a second lateral wall, and defines a plurality of pockets, a plurality of pocket supports, an interior chamber, a plurality of windows, and a recess. A pocket support of the plurality of pocket supports is disposed within each pocket of the plurality of pockets. A first mask includes an elongate member and a plurality of projections and is integrally formed with the medical device main body. The mask is used for performing a finishing process on the device and subsequently removed using a tool.

16 Claims, 14 Drawing Sheets

(51) Int. Cl.
  *B33Y 80/00* (2015.01)
  *B24B 1/00* (2006.01)
  *A61F 2/44* (2006.01)
  *B33Y 10/00* (2015.01)

(52) U.S. Cl.
  CPC .............. *B33Y 40/20* (2020.01); *B33Y 80/00* (2014.12); *A61F 2/30749* (2013.01); *A61F 2/30771* (2013.01); *A61F 2/447* (2013.01); *A61F 2/4455* (2013.01); *A61F 2002/3093* (2013.01); *A61F 2002/3097* (2013.01); *A61F 2002/30904* (2013.01); *A61F 2002/30952* (2013.01); *A61F 2002/30957* (2013.01); *A61F 2002/30962* (2013.01); *A61F 2002/30968* (2013.01); *A61F 2002/30978* (2013.01); *A61F 2002/30985* (2013.01); *A61F 2310/00023* (2013.01); *B33Y 10/00* (2014.12)

(56) References Cited

U.S. PATENT DOCUMENTS

| | | | |
|---|---|---|---|
| 5,716,412 A * | 2/1998 | DeCarlo, Jr. | B23K 26/364 623/23.5 |
| 5,961,554 A | 10/1999 | Janson et al. | |
| 5,980,572 A | 11/1999 | Kim et al. | |
| 6,102,950 A | 8/2000 | Vaccaro | |
| 6,129,763 A | 10/2000 | Chauvin et al. | |
| 6,176,882 B1 | 1/2001 | Biedermann et al. | |
| 6,375,682 B1 | 4/2002 | Fleischmann et al. | |
| 6,443,989 B1 | 9/2002 | Jackson | |
| 6,491,724 B1 | 12/2002 | Ferree | |
| 6,558,424 B2 | 5/2003 | Thalgott | |
| 6,562,074 B2 | 5/2003 | Gerbec et al. | |
| 6,685,742 B1 | 2/2004 | Jackson | |
| 6,743,257 B2 | 6/2004 | Castro | |
| 6,761,739 B2 | 7/2004 | Shepard | |
| 7,018,415 B1 | 3/2006 | McKay | |
| 7,037,339 B2 | 5/2006 | Houfburg | |
| 7,094,257 B2 | 8/2006 | Mujwid et al. | |
| 7,137,997 B2 | 11/2006 | Paul | |
| 7,220,280 B2 | 5/2007 | Kast et al. | |
| 7,396,365 B2 | 7/2008 | Michelson | |
| 7,708,779 B2 | 5/2010 | Edie et al. | |
| D629,104 S | 12/2010 | Calverley et al. | |
| 7,875,078 B2 | 1/2011 | Wysocki et al. | |
| 7,875,080 B2 | 1/2011 | Puno et al. | |
| 8,025,680 B2 | 9/2011 | Hayes et al. | |
| 8,057,548 B2 | 11/2011 | Abernathie et al. | |
| 8,062,375 B2 | 11/2011 | Glerum et al. | |
| 8,114,092 B2 | 2/2012 | Altarac et al. | |
| 8,267,939 B2 | 9/2012 | Cipoletti et al. | |
| 8,303,879 B2 | 11/2012 | Bertele et al. | |
| 8,328,872 B2 | 12/2012 | Duffield et al. | |
| 8,394,145 B2 | 3/2013 | Weiman | |
| 8,425,604 B2 | 4/2013 | Trieu | |
| D682,427 S | 5/2013 | Farris et al. | |
| 8,496,706 B2 | 7/2013 | Ragab et al. | |
| 8,496,713 B2 | 7/2013 | Bennett et al. | |
| 8,506,629 B2 | 8/2013 | Weiland | |
| 8,518,120 B2 | 8/2013 | Glerum et al. | |
| 8,523,910 B2 | 9/2013 | Seifert et al. | |
| 8,545,566 B2 | 10/2013 | Niemiec et al. | |
| 8,551,176 B2 | 10/2013 | Ullrich, Jr. et al. | |
| 8,556,974 B2 | 10/2013 | Suh et al. | |
| 8,556,979 B2 | 10/2013 | Glerum et al. | |
| 8,597,355 B2 | 12/2013 | Hansell | |
| 8,597,359 B2 | 12/2013 | Butler | |
| 8,617,244 B2 | 12/2013 | Reichen et al. | |
| 8,632,593 B2 | 1/2014 | Suh et al. | |
| 8,641,768 B2 | 2/2014 | Duffield et al. | |
| 8,679,183 B2 | 3/2014 | Glerum et al. | |
| 8,685,098 B2 | 4/2014 | Glerum et al. | |
| 8,696,751 B2 | 4/2014 | Ashley et al. | |
| 8,709,086 B2 | 4/2014 | Glerum et al. | |
| 8,888,853 B2 | 11/2014 | Glerum et al. | |
| 8,888,854 B2 | 11/2014 | Glerum et al. | |
| 8,900,309 B2 | 12/2014 | James et al. | |
| 8,926,704 B2 | 1/2015 | Glerum et al. | |
| 8,967,078 B2 * | 3/2015 | Soucy | B24B 31/00 29/451 |
| 8,992,619 B2 * | 3/2015 | Patterson | A61F 2/4455 623/17.11 |
| 9,039,771 B2 | 5/2015 | Glerum et al. | |
| 9,119,730 B2 | 9/2015 | Glerum et al. | |
| 9,155,628 B2 | 10/2015 | Glerum et al. | |
| 9,204,974 B2 | 12/2015 | Glerum et al. | |
| 9,211,196 B2 | 12/2015 | Glerum et al. | |
| 9,216,095 B2 | 12/2015 | Glerum et al. | |
| 9,216,096 B2 | 12/2015 | Lynn et al. | |
| 9,226,836 B2 | 1/2016 | Glerum | |
| 9,358,126 B2 | 6/2016 | Glerum et al. | |
| 9,358,128 B2 | 6/2016 | Glerum et al. | |
| 9,452,063 B2 | 9/2016 | Glerum et al. | |
| 9,456,903 B2 | 10/2016 | Glerum et al. | |
| 9,492,287 B2 | 11/2016 | Glerum et al. | |
| 9,510,954 B2 | 12/2016 | Glerum et al. | |
| 9,597,200 B2 | 3/2017 | Glerum et al. | |
| 9,655,745 B2 * | 5/2017 | Patterson | B23K 26/362 |
| 9,655,747 B2 | 5/2017 | Glerum et al. | |
| 9,757,248 B2 | 9/2017 | Chokshi | |
| 9,848,997 B2 | 12/2017 | Glerum et al. | |
| 9,949,841 B2 | 4/2018 | Glerum et al. | |
| 9,962,271 B2 | 5/2018 | Glerum | |
| 10,052,213 B2 | 8/2018 | Glerum et al. | |
| 10,098,758 B2 | 10/2018 | Matthews et al. | |
| 10,687,956 B2 * | 6/2020 | Ullrich, Jr. | A61F 2/4465 |
| 2004/0102850 A1 | 5/2004 | Shepard | |
| 2005/0149192 A1 | 7/2005 | Zucherman et al. | |
| 2007/0032871 A1 | 2/2007 | Michelson | |
| 2007/0073400 A1 | 3/2007 | Paul | |
| 2007/0270968 A1 | 11/2007 | Baynham et al. | |
| 2007/0293948 A1 | 12/2007 | Bagga et al. | |
| 2008/0306596 A1 | 12/2008 | Jones et al. | |
| 2009/0076616 A1 | 3/2009 | Duggal et al. | |
| 2009/0099659 A1 | 4/2009 | Oh et al. | |
| 2009/0171461 A1 | 7/2009 | Conner et al. | |
| 2009/0198278 A1 | 8/2009 | Shibata et al. | |
| 2010/0262244 A1 * | 10/2010 | Savage-Erickson | A61F 2/442 623/17.16 |
| 2010/0286779 A1 | 11/2010 | Thiobodeau | |
| 2010/0305704 A1 | 12/2010 | Messerli et al. | |
| 2011/0040384 A1 | 2/2011 | Junn et al. | |
| 2011/0160860 A1 | 6/2011 | Johnston et al. | |
| 2011/0172769 A1 | 7/2011 | Ganem et al. | |
| 2011/0172774 A1 | 7/2011 | Varela | |
| 2011/0184522 A1 | 7/2011 | Melkent et al. | |
| 2011/0190888 A1 | 8/2011 | Bertle et al. | |
| 2011/0224796 A1 | 9/2011 | Weiland et al. | |
| 2011/0307016 A1 | 12/2011 | Regies et al. | |
| 2012/0078370 A1 | 3/2012 | James et al. | |
| 2012/0089191 A1 | 4/2012 | Altarac et al. | |
| 2012/0136443 A1 | 5/2012 | Wenzel | |
| 2012/0316649 A1 | 12/2012 | Johnston et al. | |
| 2013/0030544 A1 | 1/2013 | Studer | |
| 2013/0060336 A1 | 3/2013 | Hooper et al. | |
| 2013/0060339 A1 | 3/2013 | Duffield et al. | |
| 2013/0131726 A1 | 5/2013 | Suh et al. | |
| 2013/0144388 A1 | 6/2013 | Emery et al. | |
| 2013/0158667 A1 | 6/2013 | Tabor et al. | |
| 2013/0158669 A1 | 6/2013 | Sungarian et al. | |
| 2014/0012382 A1 | 1/2014 | Doty | |
| 2014/0163682 A1 | 6/2014 | Lott et al. | |
| 2014/0163683 A1 | 6/2014 | Seifert et al. | |
| 2014/0236297 A1 | 8/2014 | Iott et al. | |
| 2014/0277474 A1 | 9/2014 | Robinson et al. | |
| 2014/0277508 A1 | 9/2014 | Baynham | |
| 2015/0100128 A1 | 4/2015 | Glerum et al. | |
| 2015/0100129 A1 | 4/2015 | Waugh et al. | |
| 2015/0272743 A1 | 10/2015 | Jimenez et al. | |
| 2015/0282941 A1 | 10/2015 | Chokshi | |
| 2015/0342749 A1 | 12/2015 | Baynham | |
| 2016/0045328 A1 | 2/2016 | Matthews et al. | |
| 2016/0184108 A1 | 6/2016 | Glerum et al. | |

(56) References Cited

U.S. PATENT DOCUMENTS

| | | | |
|---|---|---|---|
| 2016/0199193 A1* | 7/2016 | Willis | B22F 3/24 623/17.16 |
| 2016/0242927 A1 | 8/2016 | Seifert et al. | |
| 2017/0035577 A1 | 2/2017 | Iott et al. | |
| 2017/0156885 A1 | 6/2017 | Zur et al. | |
| 2017/0281432 A1 | 10/2017 | Glerum et al. | |
| 2017/0304071 A1 | 10/2017 | Black et al. | |
| 2017/0312094 A1 | 11/2017 | Chokshi | |
| 2017/0333203 A1 | 11/2017 | Glerum et al. | |
| 2018/0049886 A1 | 2/2018 | Black et al. | |
| 2018/0071108 A1 | 3/2018 | Glerum et al. | |
| 2018/0207002 A1 | 7/2018 | Glerum et al. | |
| 2018/0289508 A1 | 10/2018 | Glerum | |
| 2018/0338840 A1 | 11/2018 | Glerum et al. | |

FOREIGN PATENT DOCUMENTS

| | | |
|---|---|---|
| EP | 2025307 | 2/2009 |
| EP | 2942036 | 11/2015 |
| WO | WO2011047230 | 4/2011 |
| WO | WO2013152257 | 10/2013 |
| WO | WO2013158960 | 10/2013 |
| WO | WO2014028635 | 2/2014 |
| WO | WO2014071268 | 5/2014 |
| WO | WO2014093430 | 6/2014 |
| WO | WO2014151165 | 9/2014 |
| WO | WO2014165319 | 10/2014 |
| WO | WO2015198335 | 12/2015 |
| WO | WO2017189416 | 11/2017 |

OTHER PUBLICATIONS

Aesculap Implant Systems, "CeSpaceXP Interbody System," p. 1, accessed Apr. 24, 2014, http://www.aesculapimplantsystems.com/default.aspx?pageid=3945.

Synthes Spine, "Advanced ACF Spacer: An allograft spacer with demineralized surfaces for anterior cervical interbody fusion," Synthes.com, 2004, pp. 1-7.

Lemke, Johannes, et al., "Polyetheretherketone (PEEK) Spacers for Anterior Cervical Fusion: A Retrospective Comparative Effectiveness Clinical Trial," Open Orthop. J. 2011; 5: 348-353.

Bonovo Orthopedics, "NuVasive PCM Cervical Disc," pp. 1-9, accessed Feb. 26, 2014, http://www.bonovo-ortho.com/Products/Spine(Cervical).php.

Depuy Spine, "Surgical Technique: VG2 Cervical Allograft," Brochure from Depuy Spine, Virginia Beach, VA, 2003.

Globus Medical, "Sustain & Sustain-R, Large, Trapezoidal thoracolumbar vertebral body replacement device," pp. 1-3, accessed Feb. 26, 2014, http://www.globusmedical.com/portfolio/sustain-sustain-r-large/.

Globus Medical, "Colonial, cervical interbody fusion device," pp. 1-2, accessed Feb. 26, 2014, http://globusmedical.com/portfolio/colonial/.

*Globus Medical Inc.* v. *Depuy Synthes Products, LLC, Depuy Synthes Sales, Inc.*, Complaint, Case No. 1:13-cv-00854-UNA, at pp. 1-5 (D. Del. May 15, 2013).

Ho, Cheng, et al., "Kurokawa-type Laminoplasty using Hydroxyapatite Spacer for Cervical Myelopathy," Hong Kong J. Orthop. Surg. 2004: 8 (1):12-21.

Mahe Medical, "Perfect Spine, Vertebral Spacer System," from www.slideshare.net, slide No. 10, accessed Feb. 26, 2014, http://image.slidesharecdn.com/cages-130721071738-phpapp02/95/slide-10-638.jpg?cb=1374409152.

Niu, Chi-Chien et al., "Trapezoidal Titanium Cage in Anterior Cervical Interbody Fusion: A Clinical Experience," Chang Gung Med. J. Apr. 2005; 28 (4): 212-221.

Nutech Medical, "Interbody," Nutchmedical.com, pp. 1-3, accessed Feb. 26, 2014, http://nutechmedical.com/products/spine/interbody/.

United States Patent and Trademark Office, Office Action for U.S. Appl. No. 86/253,948, Applicant: DeGen Medical, Inc., dated Dec. 29, 2014, pp. 33, 39, 42, 53 and 54.

Gelisim Medical, "Spinal Cerrahi", Gelisimmedikal.com, pp. 1-2, 2013, accessed Jun. 27, 2014, http://www.gelisimmedikal.com/eng/servical-peek-cage.asp.

International Bureau. "International Preliminary Report on Patentability" for application No. PCT/2017/029092, dated Oct. 30, 2018, pp. 1-6.

International Searching Authority, "Notification of Transmittal of the International Search and the Written Opinion of the International Search Authority, or the Declaration" for application No. PCT/US2017/029092, dated Jul. 24, 2017, pp. 1-12.

English translation of "Abstract" of application No. CN101049254, retreived from Lexus TotalPatent One on Jun. 6, 2017.

* cited by examiner

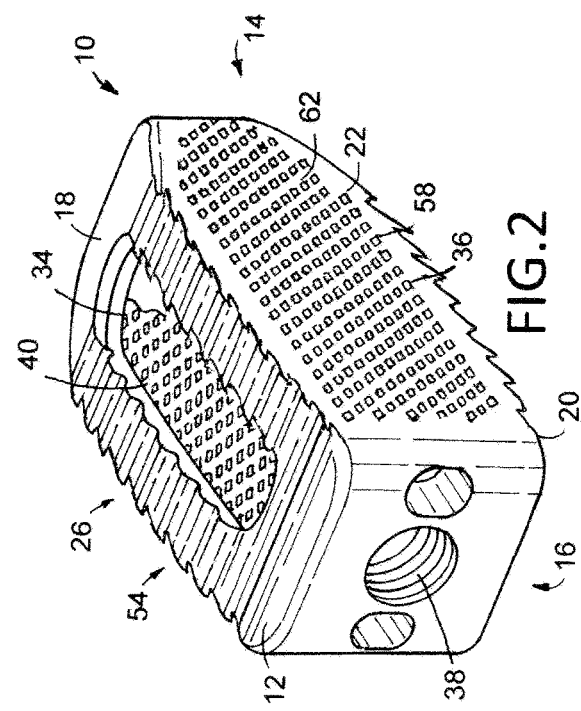
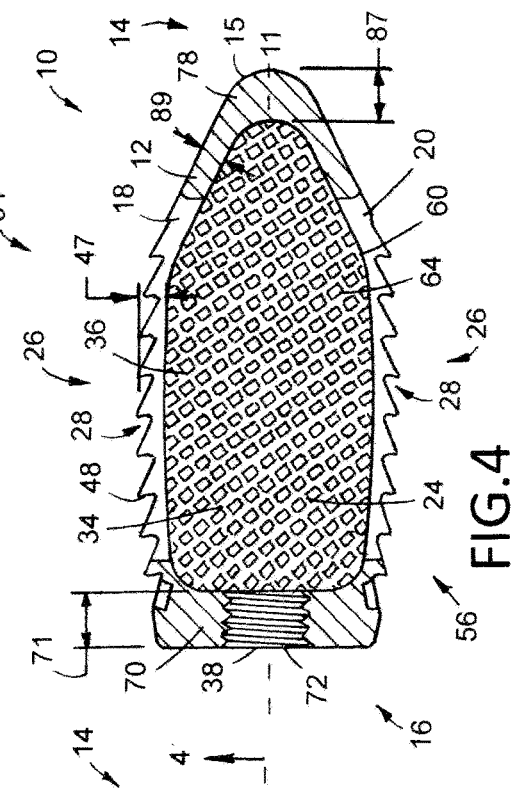
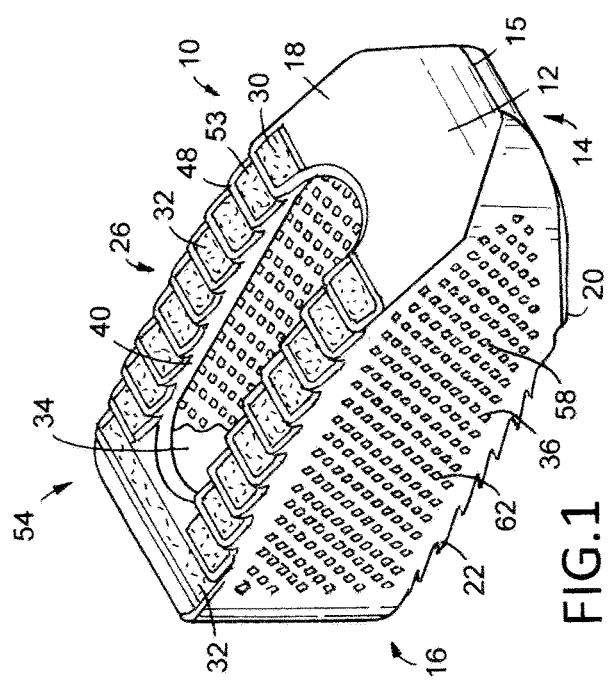
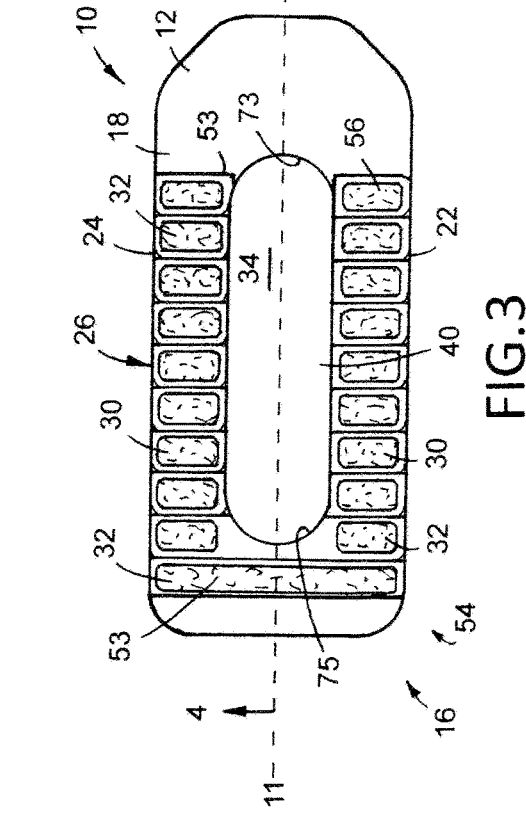

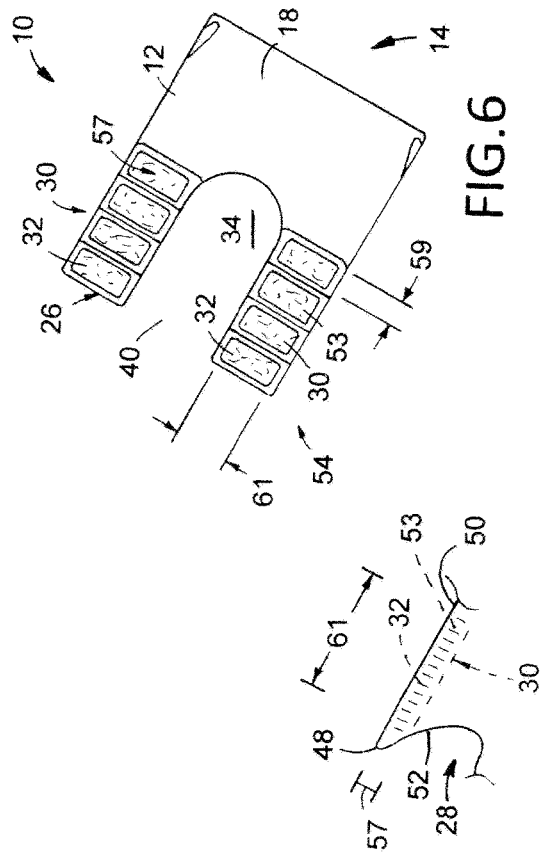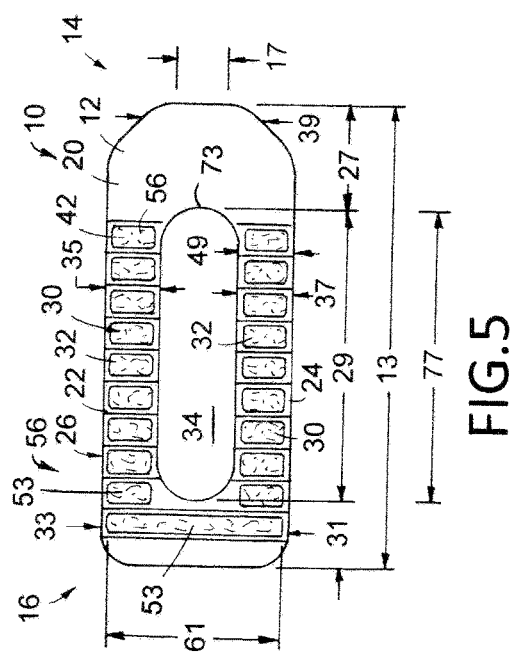

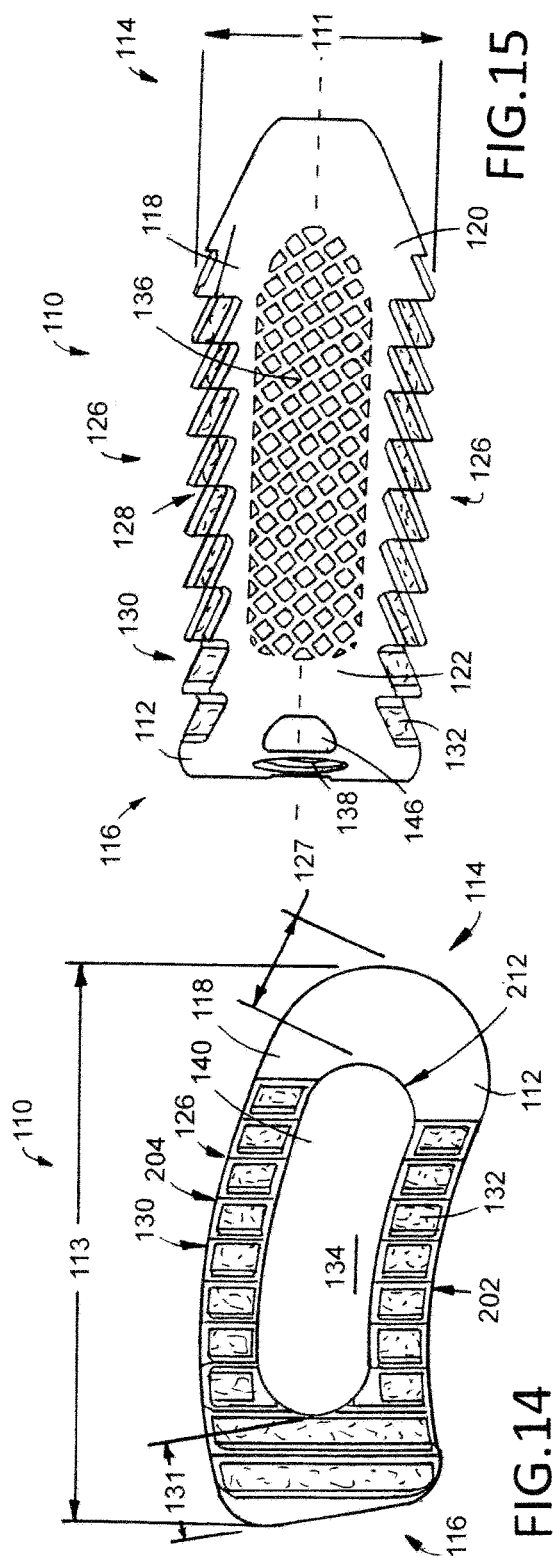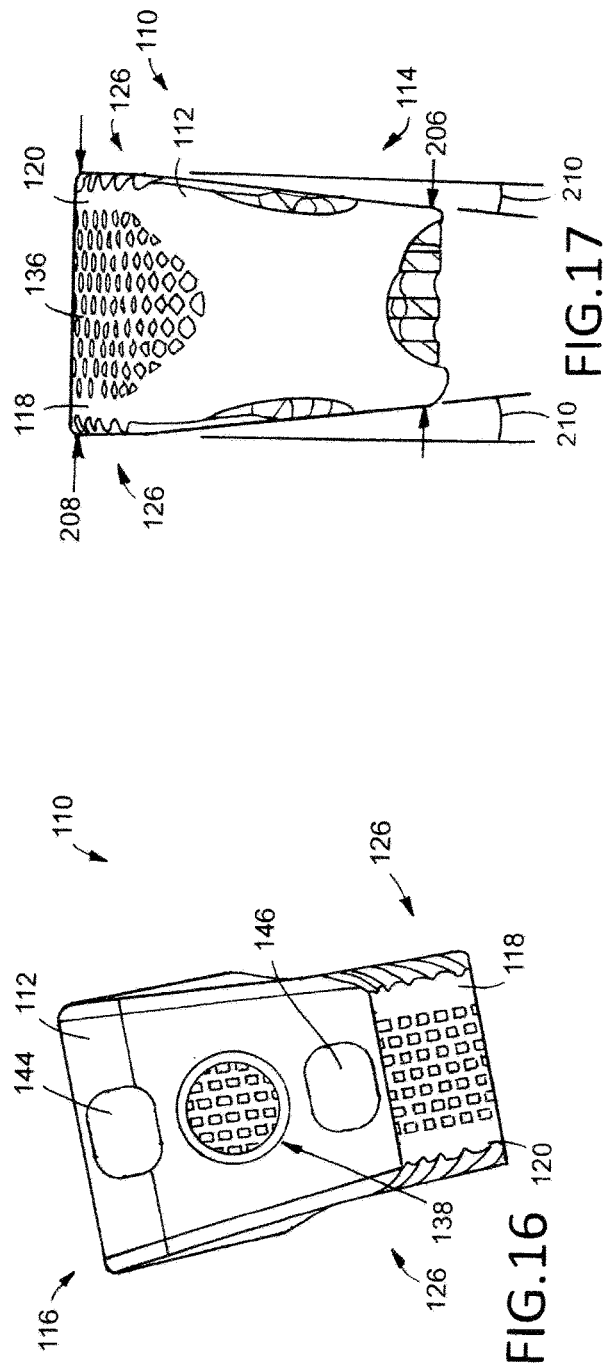

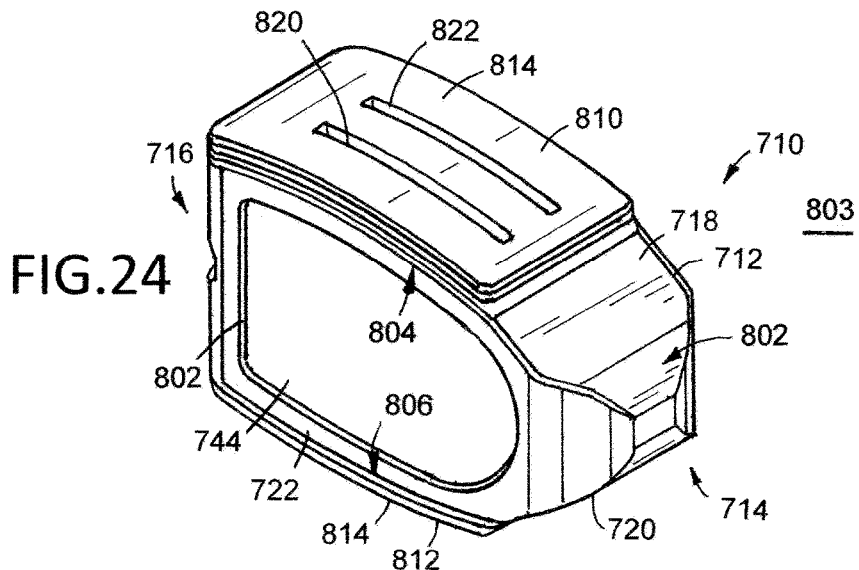
FIG.24
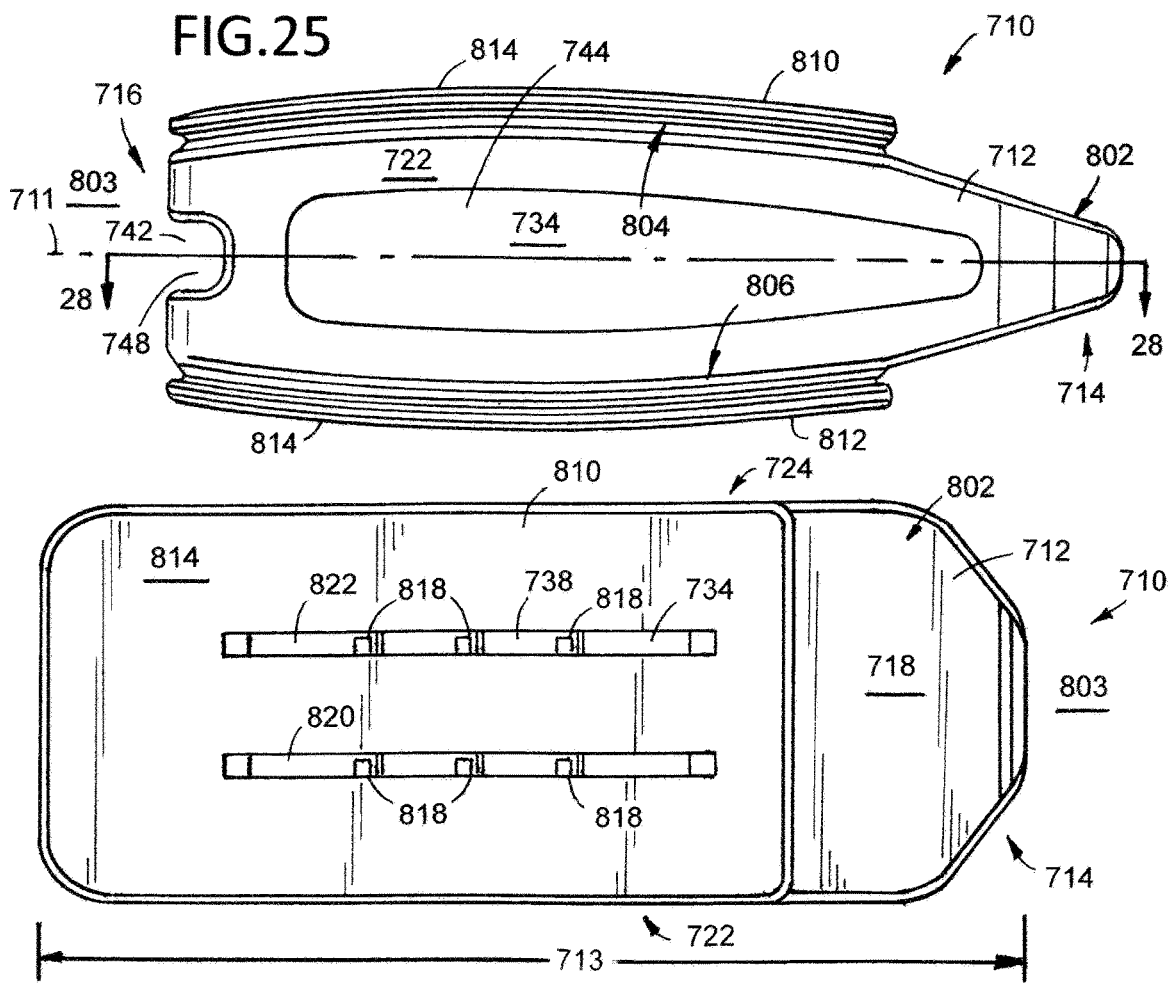
FIG.25
FIG.26

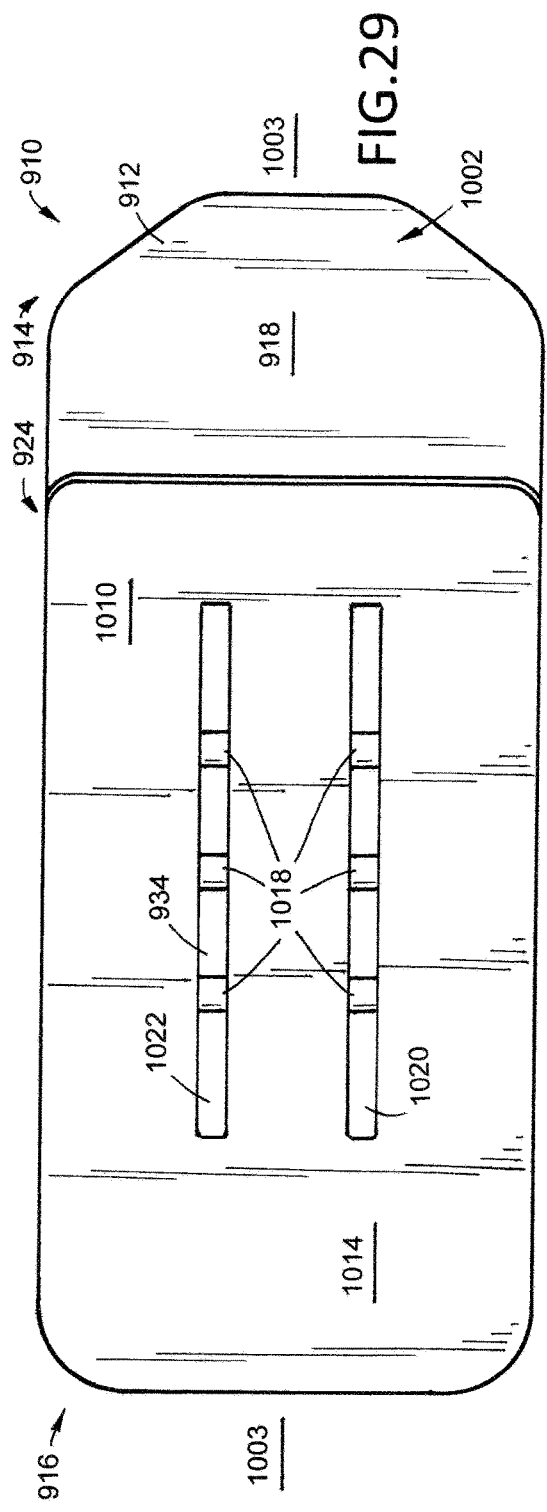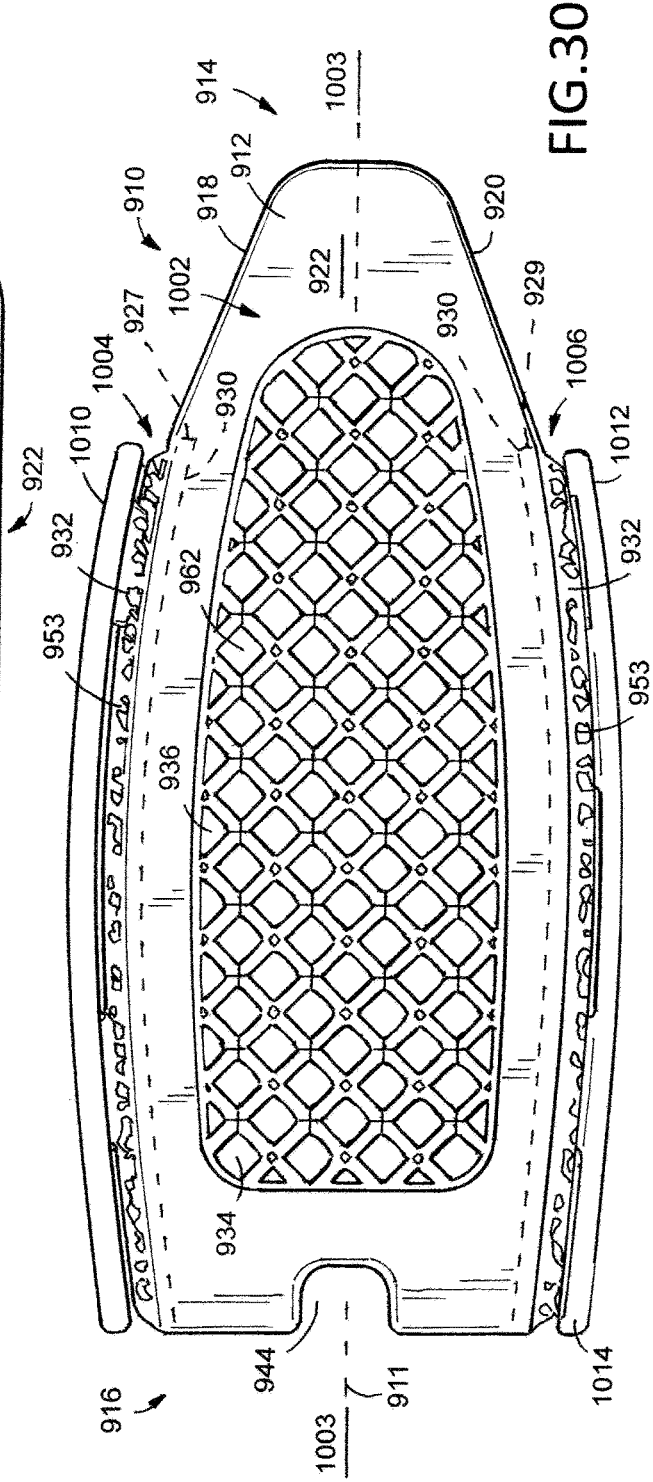

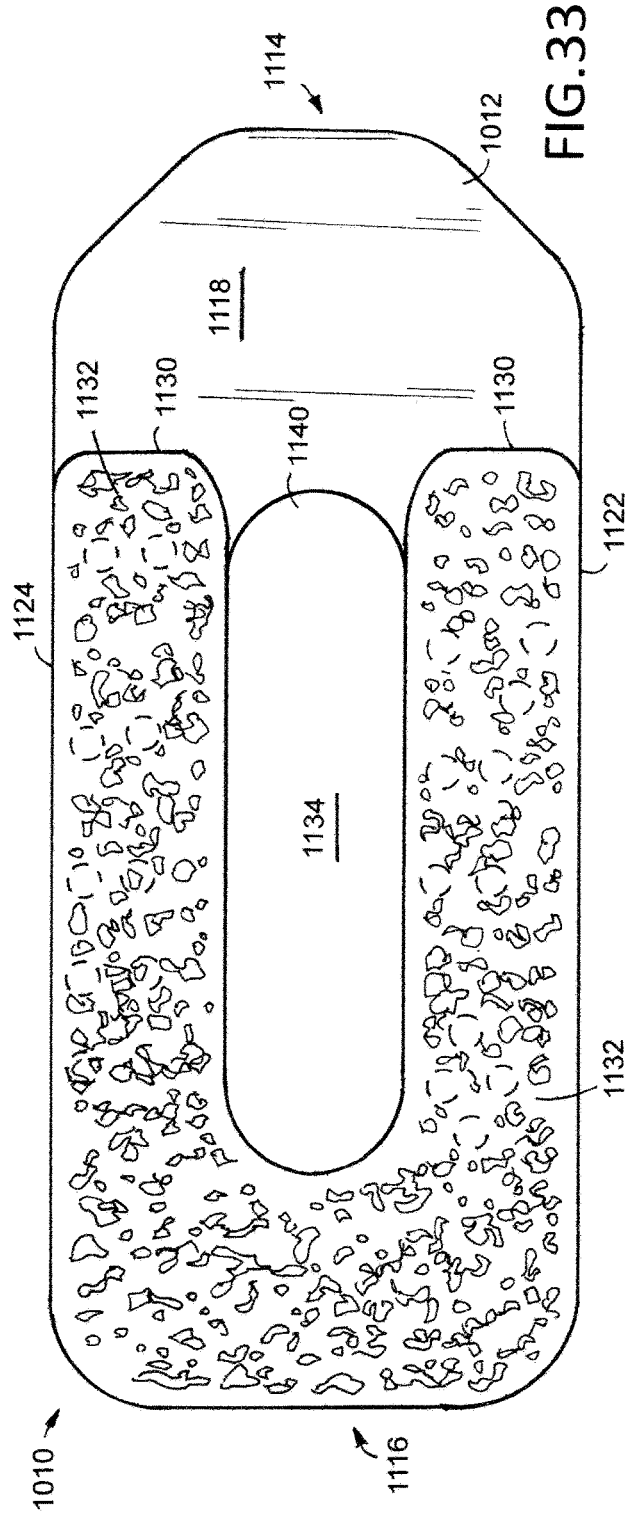
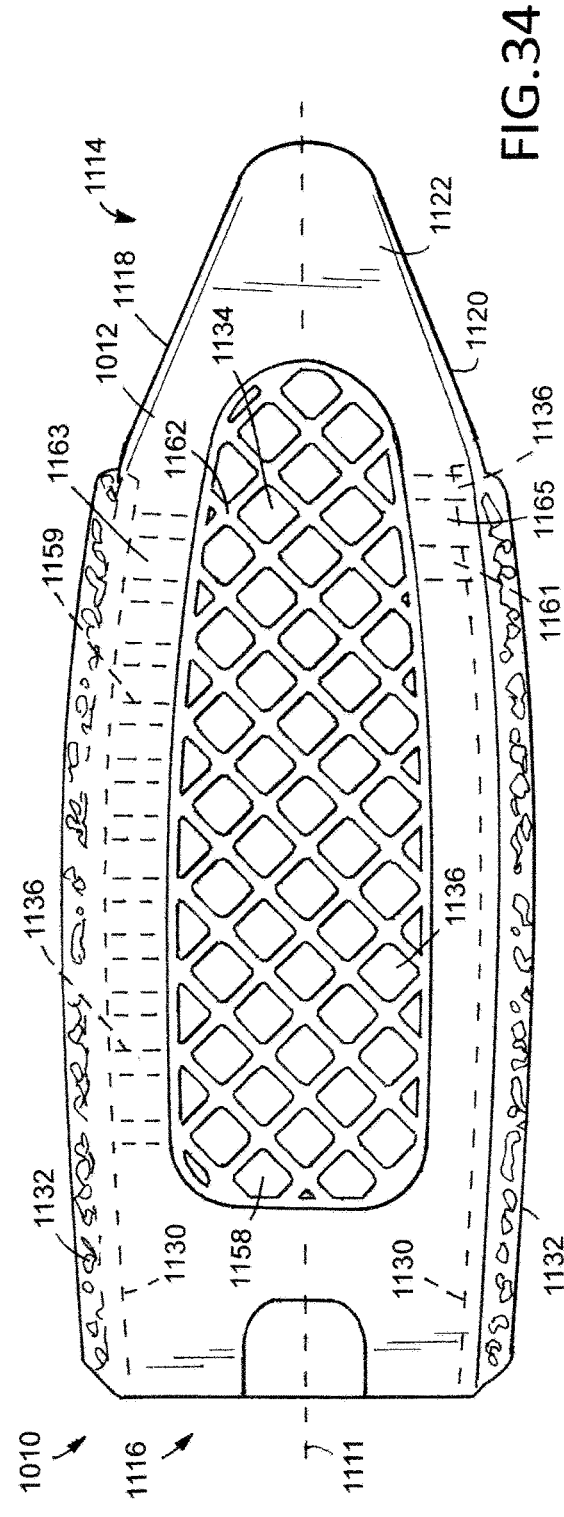

METHODS OF MAKING MEDICAL DEVICES

RELATED APPLICATION

This application claims the benefit of U.S. Provisional Application No. 62/558,492, filed on Sep. 14, 2017. The entire disclosure of this related application is hereby incorporated into this disclosure by reference.

FIELD

The disclosure relates generally to the field of medical devices. Specific examples relate to implantable medical devices, such as implantable medical devices suitable for implantation in spaces between vertebrae in a vertebral column of an animal. The disclosure also relates to medical device precursors and methods of making medical devices.

BACKGROUND

Over time, bone may degenerate as a result of trauma, disease, and natural processes, such as aging. Bone degeneration can affect surrounding tissues and have a significant negative impact on the lifestyle of an animal. For example, destabilization of a spine in a vertebrate, such as a human being, may result in alteration of the spacing between adjacent vertebrae. This can place pressure on nerves that pass between the vertebral bodies. In turn, this pressure can cause pain, discomfort, and, eventually, nerve damage.

One way to alleviate the pain and discomfort that occurs after the degeneration or destabilization of a portion of the spine is to implant a medical device into the space between two adjacent vertebrae. Implanted in this manner, the medical device supports the structure of the spine by maintaining a desired spacing between the adjacent vertebrae. The medical device can facilitate the fusion of the adjacent vertebrae, too.

One challenge in designing implantable medical devices intended for placement between vertebrae is balancing performance and handling needs. The need for a structure that provides desired functionality, capabilities, and characteristics often seems at odds with the need for a structure that is easy to work with during implantation. While new manufacturing technologies have developed in recent years, this same design and development challenge for these implantable medical devices remains. Indeed, while these new technologies enhance the rate at which new designs can be prototyped and new devices can be produced, even recent examples of devices in the art suffer drawbacks that stem from this basic design and development challenge. For example, recent examples of implantable medical devices intended for placement between vertebrae that are produced with additive manufacturing technologies sacrifice functionality to achieve desired handling characteristics. Furthermore, while these new manufacturing technologies provide new design opportunities, they also present new challenges as they are used with existing processing, handling, and other manufacturing workflows.

A need exists, therefore, for improved medical devices and methods of making medical devices.

SUMMARY OF SELECTED EXAMPLE EMBODIMENTS

Various example medical devices and methods of making a medical device are described herein.

An example medical device includes a main body that has a proximal end, a distal end, an upper wall, a lower wall, a first lateral wall, a second lateral wall, and defines a plurality of teeth, a pocket that extends into the main body on a tooth of the plurality of teeth, a support element that is disposed within the pocket and extends across the pocket, an interior chamber, a plurality of windows, and a first passageway that extends from the distal end toward the proximal end. A first set of teeth of the plurality of teeth extends from the upper wall and away from the lower wall. A second set of teeth of the plurality of teeth extends from the lower wall and away from the upper wall. A first set of windows of the plurality of windows extends through the first lateral wall and provides access to the interior chamber. A second set of windows of the plurality of windows extends through the second lateral wall and provides access to the interior chamber. The first set of windows defines a first wall support and the second set of windows defines a second wall support. Each of the first wall support and the second wall support is different than the support element.

An example method of making a medical device comprises: creating a model of a medical device; uploading the model to a manufacturing system, such as a 3D-printing system; initiating manufacture of the medical device; and removing the medical device from the manufacturing system.

Another example method of making a medical device comprises: creating a medical device precursor, the medical device precursor includes a medical device main body and a mask attached to the main body, the medical device main body has a first portion exposed to an environment exterior to the medical device main body and a second portion disposed adjacent the mask and shielded from the environment exterior to the medical device main body by the mask; performing a finishing process on the medical device precursor; and separating the mask from the medical device main body to produce a medical device.

Additional understanding of the example medical devices, medical device precursors, and methods of making medical devices can be obtained by reviewing the detailed description, below, and the appended drawings.

BRIEF DESCRIPTION OF THE DRAWINGS

FIG. 1 is a perspective view of an example implantable medical device.

FIG. 2 is another perspective view of the implantable medical device illustrated in FIG. 1.

FIG. 3 is a top view of the implantable medical device illustrated in FIG. 1.

FIG. 4 is a cross-sectional view of the implantable medical device illustrated in FIG. 3 taken along Line 4-4.

FIG. 5 is a bottom view of the implantable medical device illustrated in FIG. 1.

FIG. 6 is another perspective view of the implantable medical device illustrated in FIG.

FIG. 7 is a partially broken away rear view of the implantable medical device illustrated in FIG. 1.

FIG. 8 is a partially broken away side view of the implantable medical device illustrated in FIG. 1.

FIG. 9 is a magnified view of area 9 indicated in FIG. 8.

FIG. 9A is a magnified view of area 9A indicated in FIG. 9.

FIG. 14 is another top view of the implantable medical device illustrated in FIG. 10.

FIG. 15 is a side view of the implantable medical device illustrated in FIG. 10.

FIG. 16 is a rear view of the implantable medical device illustrated in FIG. 10.

FIG. 17 is a partially broken away front view of the implantable medical device illustrated in FIG. 10.

FIG. 24 is a perspective view of an example medical device precursor that includes a medical device main body, a first mask, and a second mask.

FIG. 25 is an elevation view of the medical device precursor illustrated in FIG. 24.

FIG. 26 is a top view of the medical device precursor illustrated in FIG. 24.

FIG. 29 is a top view of another example medical device precursor that includes a medical device main body, a first mask, and a second mask.

FIG. 30 is an elevation view of the medical device precursor illustrated in FIG. 29.

FIG. 33 is a top view of another example medical device subsequent to the separation of the first and second masks from the medical device main body.

FIG. 34 is an elevation view of the medical device illustrated in FIG. 33.

DETAILED DESCRIPTION

Figure 11:
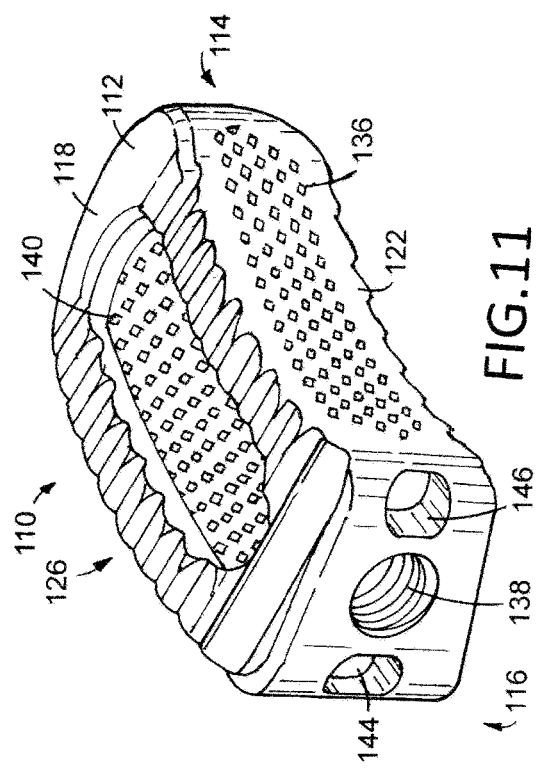
FIG. 11 is another perspective view of the implantable medical device illustrated in FIG. 10.
Figure 13:
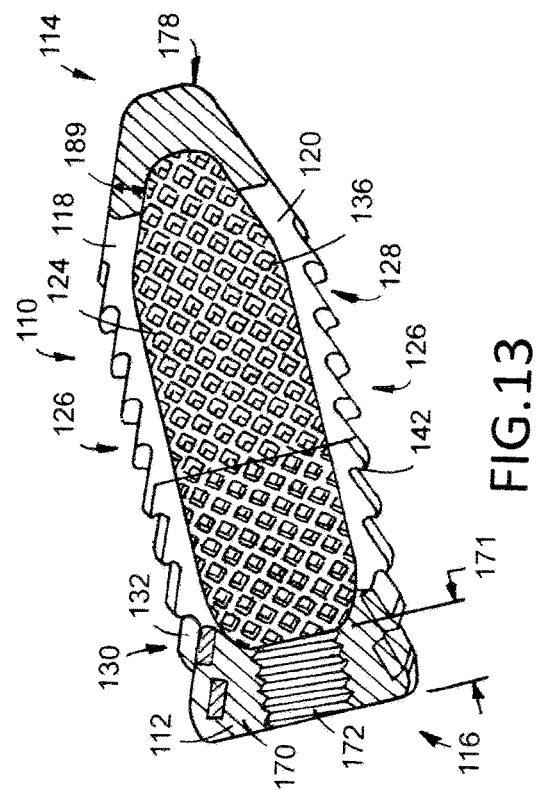
FIG. 13 is a cross-sectional view of the implantable medical device illustrated in FIG. 12 taken along Line 13-13.
Figure 10:
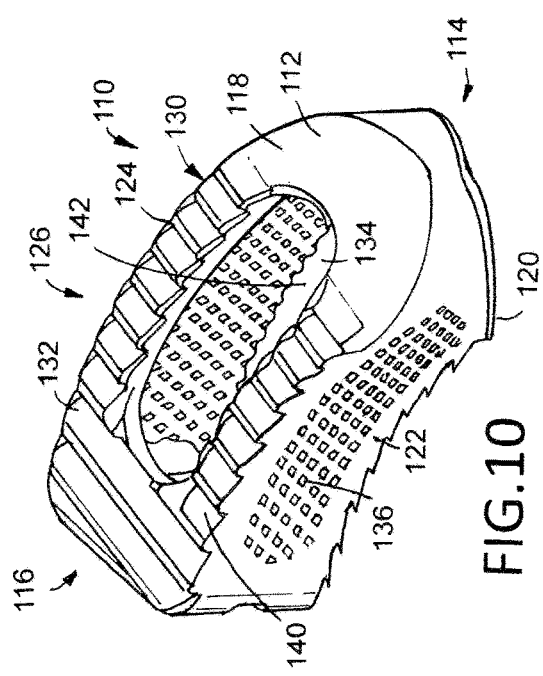
FIG. 10 is a perspective view of another example implantable medical device.
Figure 12:
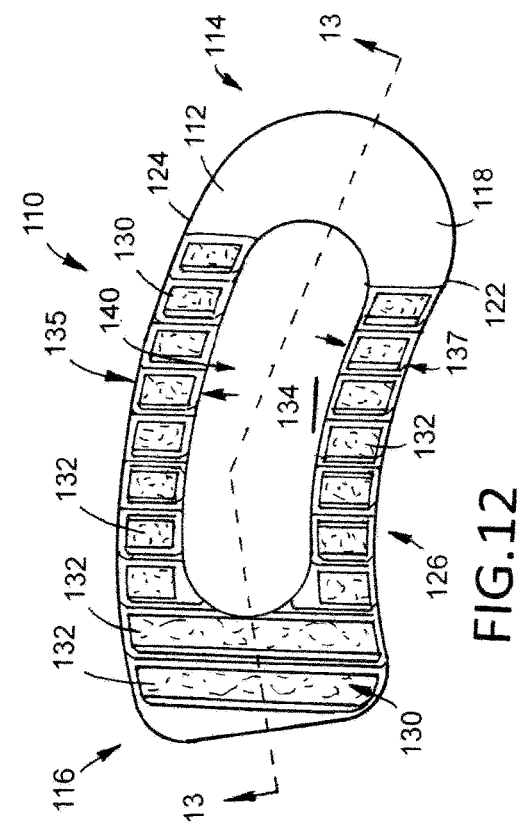
FIG. 12 is a top view of the implantable medical device illustrated in FIG. 10.

The following detailed description and the appended drawings describe and illustrate various example embodiments of medical devices, medical device precursors, and methods of making medical devices. The description and illustration of these examples are provided to enable one skilled in the art to make and use a medical device, a medical device precursor, and to practice a method of making a medical device. They are not intended to limit the scope of the claims in any manner.

Some of the example medical devices described herein are useful in the maintaining of support between vertebrae in a vertebral column of an animal. For example, some of the example medical devices described herein can comprise intervertebral spacers that are suitable for use implantation within various intervertebral spaces along a vertebral column of a human to assist in the maintaining of a desired spacing between adjacent vertebrae. Some of the example medical devices are sized and configured for implantation between adjacent vertebrae of a human.

FIGS. 1, 2, 3, 4, 5, 6, 7, 8, 9, and 9A illustrate an example implantable medical device 10. The implantable medical device 10 includes a main body 12 that has a lengthwise axis 11, a proximal end 14, a distal end 16, a length 13 that extends from the proximal end 14 to the distal end 16, an upper wall 18, a lower wall 20, a first lateral wall 22, a second lateral wall 24, and defines a plurality of teeth 26, a plurality of gullets 28, a plurality of pockets 30, a plurality of support elements 32, an interior chamber 34, a plurality of windows 36, a first passageway 38, a second passageway 40, a third passageway 42, a first recess 44, and a second recess 46. In the illustrated embodiment, the length 13 is equal to about 27 millimeters.

In the illustrated embodiment, the proximal end 14 is rounded between the upper wall 18 and the lower wall 20 and has a radius of curvature 15, as shown best in FIGS. 1, 4, and 8, and a width 17, as shown best in FIG. 5. The proximal end 14 can have any suitable radius of curvature 15, such as those between about 0.8 millimeters and about 3.2 millimeters. The proximal end 14 can have any suitable width 17, such as those equal to about 3 millimeters. The distal end 16 has a width 19, as shown best in FIG. 7. The distal end 16 can have any suitable width 19, such as those equal to about 11 millimeters. However, alternative embodiments can have a distal end that has a width equal to, greater than, less than, or about 9 millimeters (e.g., for PLIF or TLIF), 11 millimeters (e.g., for PLIF or TLIF), or between about 9 millimeters and about 11 millimeters, or between about 8 millimeters and about 13 millimeters.

In the illustrated embodiment, each of the upper wall 18 and the lower wall 20 extends away from the lengthwise axis 11 as it extends from the proximal end 14 toward the distal end 16 and extends toward the lengthwise axis 11 as it extends from a location between the proximal end 14 and the distal end 16 to the distal end 16. This results in a main body 12 that has a first height 21 at the proximal end 14, a second height 23 between the proximal end 14 and the distal end 16, and a third height 25 at the distal end 16, as shown in FIG. 8. The first height 21 is less than the second height 23 and the second height 23 is greater than the third height 25. In the illustrated embodiment, the second height 23 can be any suitable height, such as those between about 7.875 millimeters and about 16.125 millimeters. As shown in FIG. 5, each of the upper wall 18 and the lower wall 20 has a first length 27, a second length 29, a third length 31, a first width 33, a second width 35, a third width 37, and a fourth width 39. The first length 27 extends from the proximal end 14 to a passageway (e.g., second passageway 40, third passageway 42). The second length 29 extends from a proximal end of a passageway (e.g., second passageway 40, third passageway 42) to a distal end of the passageway (e.g., second passageway 40, third passageway 42). The third length 31 extends from the distal end of the passageway (e.g., second passageway 40, third passageway 42) to the distal end 16.

Each of the first length 27, the second length 29, and the third length 31 is measured along the lengthwise axis 11 and can be any suitable length. Each of the first length 27 and the third length 31 is less than the second length 29 and the first length 27 is greater than the third length 31. In the illustrated embodiment, the first length 27 is equal to about 6 millimeters, the second length 29 is equal to about 17 millimeters, and the third length 31 is equal to about 4 millimeters. However, alternative embodiments can include a main body that has any suitable first length, second length, and/or third length. For example, a main body can have a first length that is equal to, greater than, less than, or about 6 millimeters, or between about 4 millimeters and about 8 millimeters, a second length equal to, greater than, less than, or about 17 millimeters, or between about 12 millimeters and about 23 millimeters, and/or a third length equal to, greater than, less than, or about 4 millimeters, or between about 3 millimeters and about 5 millimeters, and any other first length, second length, and/or third length considered suitable for a particular embodiment.

The first width 33 extends from the first lateral wall 22 to the second lateral wall 24 at the distal end 16. The second width 35 extends from the first lateral wall 22 to a passageway (e.g., second passageway 40, third passageway 42). The third width 37 extends from the second lateral wall 24 to a passageway (e.g., second passageway 40, third passageway 42). The fourth width 39 extends from the first lateral wall 22 to the second lateral wall 24 between a passageway (e.g., second passageway 40, third passageway 42) and the proximal end 14. Each of the first width 33, the second width 35, the third width 37, and the fourth width 39 is measured along an axis that is perpendicular to an axis that is parallel to the lengthwise axis 11 and can have any suitable dimension. Each of the second width 35, the third width 37, and the fourth width 39 is less than the first width 33 and each of the second width 35 and the third width 37 is less than the fourth width 39. In the illustrated embodiment, each of the second width 35 and the third width 37 is equal to about 3.2 millimeters. However, alternative embodiments can include a second width and a third width that has any suitable dimension. For example, a second width and/or a third width can be equal to, greater than, less than, or about 3.2 millimeters, between about 2.4 millimeters and about 4 millimeters, or any other dimension considered suitable for a particular embodiment.

In the illustrated embodiment, each of the first lateral wall 22 and the second lateral wall 24 extends away from an axis that is parallel to the lengthwise axis 11 as it extends from the proximal end 14 toward the distal end 16 and extends toward the lengthwise axis 11 as it extends from a location between the proximal end 14 and the distal end 16 to the distal end 16. As shown in FIG. 7, each of the first lateral wall 22 and the second lateral wall 24 has a thickness 41 that extends from an exterior surface of a lateral wall to an interior surface of the lateral wall and can be any suitable thickness. In the illustrated embodiment, the thickness 41 is equal to about 1 millimeter. However, alternative embodiments can include a lateral wall that has any suitable thickness. For example, a lateral wall can have a thickness equal to, greater than, less than, or about 1 millimeter, between about 0.5 millimeters and about 1.5 millimeters, or any other dimension considered suitable for a particular embodiment.

In the illustrated embodiment, each tooth of the plurality of teeth 26 is partially disposed over a gullet of the plurality of gullets 28 and has a tip 48, a tooth back 50, a tooth face 52, an angle 43 disposed between the tooth back 50 and the tooth face 52, and a rake angle 45. The tip 48 of each tooth of the plurality of teeth 26 is disposed on a hypothetical circle that has a radius of curvature, which can be any suitable radius of curvature, such as a radius of curvature of 60 millimeters. Alternative embodiments, however, can include a plurality of teeth disposed on a hypothetical circle that has a radius of curvature that is equal to, greater than, less than, or about 60 millimeters, between about 40 millimeters and about 80 millimeters, between about 50 millimeters and about 70 millimeters, or any other radius of curvature considered suitable for a particular embodiment. The angle 43 can be any suitable angle, such as an angle equal to about 52.5 degrees. The rake angle 45 can be any suitable angle, such as an angle equal to about 22.5 degrees. The tip 48 of each tooth of the plurality of teeth 26 is disposed a distance 47 from the interior chamber 34, which can be any suitable distance, such as a distance equal to about 1.2 millimeters. However, alternative embodiments can include a plurality of teeth that has any suitable angle between a tooth back and a tooth face, a rake angle, and/or distance between an interior chamber and a tip, such as angles between a tooth back and a tooth face that are equal to greater than, less than, or about 52.5 degrees, or between about 45 degrees and about 60 degrees, rake angles that are equal to greater than, less than, or about 22.5 degrees, or between about 15 degrees and about 30 degrees, distances between a tip and an interior chamber that are equal to greater than, less than, or about 1.2 millimeters, or between about 0.5 millimeters and about 2 millimeters, and any other angle, rake angle, or distance considered suitable for a particular embodiment.

A first set of teeth 54 of the plurality of teeth 26 extends from the upper wall 18, away from the lower wall 20, and away from the proximal end 14 and a second set of teeth 56 of the plurality of teeth 26 extends from the lower wall 20, away from the upper wall 18, and away from the proximal end 14. Each of the first set of teeth 54 and the second set of teeth 56 includes eighteen teeth, nine teeth positioned on a first side of a passageway (e.g., second passageway 40, third passageway 42) and nine teeth positioned on a second side of the passageway (e.g., second passageway 40, third passageway 42). Each tooth of the first set of teeth 54 and the second set of teeth 56 is positioned on a side of a passageway (e.g., second passageway 40, third passageway 42) and has a width 49 equal to the width (e.g., second width 35, third width 37) of the portion of the wall on which it is disposed (e.g., 3.2 millimeters).

While each set of teeth has been illustrated as including eighteen teeth and each tooth has illustrated as having a width that is equal to the width of the portion on which it is disposed, a set of a plurality of teeth can include any suitable number of teeth and each tooth can have any suitable structural arrangement. Selection of a suitable number of teeth to include in a set of teeth and of a suitable structural arrangement for each tooth can be based on various considerations, including the material that forms a main body that defines a plurality of teeth. Examples of numbers of teeth to include in a set of teeth include one, more than one, two, a plurality, more than two, more than five, more than ten, and any other number considered suitable for a particular embodiment. Examples of widths considered suitable for a tooth include widths that are equal to, less than, greater than, about, or different than the width of the portion of the wall on which the tooth is disposed.

In the illustrated embodiment, a gullet of the plurality of gullets 28 is disposed adjacent each tooth of the plurality of teeth 26. As best shown in FIG. 9, each gullet of the plurality of gullets 28 has a radius of curvature 51 disposed between adjacent teeth of the plurality of teeth 26. The radius of curvature 51 can be any suitable radius of curvature, such as a radius of curvature equal to, greater than, less than, or about 0.25 millimeters, between about 0.2 millimeters and about 0.3 millimeters, and any other radius of curvature considered suitable for a particular embodiment.

In the illustrated embodiment, a pocket of the plurality of pockets 30 extends into the main body 12 on the tooth back 50 of each tooth of the plurality of teeth 26, extends between the tip 48 and the upper wall 18 with respect to the first set of teeth 54, and extends between the tip 48 and the lower wall 20 with respect to the second set of teeth 56 such that no pocket of the plurality of pockets 30 extends into the radius of curvature 51 of a gullet of the plurality of gullets 28. In addition, a pocket of the plurality of pockets 30 extends into the main body 12 between the distal end 16 and a passageway (e.g., second passageway 40, third passageway 42) on each of the upper wall 18 and the lower wall 20, which has a length greater than two times the length of a pocket that extends into the main body 12 on a tooth back 50 and does not extend into the radius of curvature 51 of a gullet of the plurality of gullets 28. Each pocket of the plurality of pockets 30 is sized and configured to receive a support element of the plurality of support elements 32 and has a depth 57, a width 59, and a length 61. The depth 57 can be any suitable depth, such as a depth equal to, greater than, less than, or about 0.5 millimeters, between about 0.3 millimeters and about 0.7 millimeters, and any other depth considered suitable for a particular embodiment. The width 59 can be any suitable width, such as a width equal to, greater than, less than, or about 2.5 millimeters, or between about 2 millimeters and about 3 millimeters, for pockets disposed on teeth disposed adjacent a passageway (e.g., second passageway 40, third passageway 42) and width equal to, greater than, less than, or about 10.3 millimeters, or between about 9 millimeters and about 11.5 millimeters, for pockets disposed between the distal end 16 and a passageway (e.g., second passageway 40, third passageway 42). The length 61 can be any suitable length, such as a length equal to, greater than, less than, or about 1.2 millimeters, between about 0.5 millimeters and about 2 millimeters, and any other length considered suitable for a particular embodiment.

While a pocket has been illustrated as being defined on each tooth of the plurality of teeth 26, a pocket can be defined on any suitable number of teeth and selection of a suitable number of teeth to include a pocket can be based on various considerations, including the type of material that forms a main body and/or the desired bone ingrowth intended to be achieved after implantation. Examples of numbers of teeth considered suitable to define a pocket include one, more than one, two, a plurality, than two, more than five, more than ten, a set of teeth, every other tooth of a plurality of teeth, every other row of teeth of a plurality of teeth, such that pockets are formed at angles to one another relative to a lengthwise axis of a main body, only proximal teeth, only distal teeth, only teeth disposed between a proximal set of teeth and a distal set of teeth, each tooth of a plurality of teeth, and any other number considered suitable for a particular embodiment.

In the illustrated embodiment, a support element of the plurality of support element 32 is disposed within each pocket of the plurality of pockets 30 and is sized and configured to promote bone ingrowth. For example, each support element of a plurality of support elements can extend along an entire length, width, and/or depth of a pocket within which it is disposed or can extend along a portion of a length, width, and/or depth that is less than the total length, width, and/or depth of a pocket within which it is disposed. A support element of the plurality of support elements 32 can include any suitable structure capable of promoting bone ingrowth. The term "support" does not impart any specific function by the term and can include any physical support, mechanical support, and/or biological support. In the illustrated embodiment, each support element of the plurality of support elements 32 is a pocket support formed of, and comprising, a mesh 53 that can be configured in any suitable manner, such as in an irregular configuration (e.g., the material forms a plurality of tunnels and/or passageways that allow for an increased bone ingrowth relative to devices that fail to include this structure, semi-porous trabecular-like mesh) or a regular configuration (e.g., gridded, latticed, the material forms a plurality of tunnels and/or passageways that allow for an increased bone ingrowth relative to devices that fail to include this structure). When a medical device is formed (e.g., using 3D-printing or any other method or technique described herein), it is considered advantageous to define the plurality of pockets in a model first and subsequently include a support element (e.g., pocket support, mesh) in each pocket. This allows for each pocket to delineate the physical boundaries within which a support element (e.g., pocket support) is disposed and within which bone ingrowth can be achieved (e.g., within the tunnels and/or passageways defined by the pocket support).

While a support element of the plurality of support element 32 has been illustrated as being disposed within each pocket of the plurality of pockets 30, a support element can be disposed in any suitable number of pockets and be formed using any suitable method or technique. Selection of a suitable number of pockets to include a support element and/or of a suitable method or technique to form a support element can be based on various considerations, including the type of material that forms a main body and/or the desired bone ingrowth intended to be achieved after implantation. Examples of numbers of pockets considered suitable to include a support element include zero, one, more than one, two, a plurality, than two, more than five, more than ten, a set of teeth, each pocket of a plurality of pockets, and any other number considered suitable for a particular embodiment. Examples of methods and techniques considered suitable to form a support element include forming a support element, or each support element, such that it is integrally formed with a main body, such that a support element is formed of the same, or a different, material as a medical device main body, such that it is formed separately of the same material, or a different material, as a main body and positioned within a pocket and attached to the main body (e.g., welding, adhesives, spray coating), etching material from a main body to form a support element, using the methods and/or techniques described herein with respect to forming a medical device main body, and any other method or technique considered suitable for a particular embodiment.

In the illustrated embodiment, a first set of windows 58 of the plurality of windows 36 extends through the first lateral wall 22 and provides access to the interior chamber 34 and a second set of windows 60 of the plurality of windows 36 extends through the second lateral wall 24 and provides access to the interior chamber 34. The first set of windows 58 defines a first wall support 62 and the second set of windows 60 defines a second wall support 64. Each of the first wall support 62 and the second wall support 64 is different than the plurality of support elements 32 and is sized and configured to promote bone ingrowth. A first wall support and a second wall support can include any suitable support capable of providing bone ingrowth. In the illustrated embodiment, the first wall support 62 is a first gridded framework and the second wall support 64 is a second gridded framework that has the same structural configuration as the first gridded support framework. Each of the first wall support 62 and the second wall support 64 extends from the distal end of the support toward the proximal end of the support and away from an axis that is parallel to the lengthwise axis 11 of the main body 12 to a location disposed between the proximal end of the support and the distal end of the support, extends from the location between the proximal end of the support and the distal end of the support and toward the axis that is parallel to the lengthwise axis 11 of the main body 12 to the proximal end of the support, and has a curved proximal end. Each of the first wall support 62 and the second wall support 64 has a first set of radii of curvature 63 disposed between the location between the proximal end of the support and the distal end of the support and the proximal end of the support and a second set of radii of curvature 65 disposed at the distal end. The radii of curvature 63 and radii of curvature 65 can have any suitable radius of curvature, such radii of curvature equal to, greater than, less than, or about 3 millimeters, 1.5 millimeters, and any other radii of curvature considered suitable for a particular embodiment.

In the illustrated embodiment, each window of the plurality of windows 36 is a rectangular prism that has a length 67, rounded corners 68, a height 69, and a depth equal to the thickness of the lateral wall through which it extends (e.g., 1 millimeter). The length 65, the height 67, and depth of a window of the plurality of windows 36 can have any suitable dimension, such as a length 65 that is equal to, greater than, less than, or about 0.65 millimeters, or between about 0.5 millimeters and about 0.8 millimeters, and a height that is equal to, greater than, less than, or about 0.65 millimeters, or between about 0.5 millimeters and about 0.8 millimeters. The rounded corners 68 can have any suitable radius of curvature, such as a radius of curvature equal to, greater than, less than, or about 0.15 millimeters, or between about 0.1 millimeters and about 0.2 millimeters.

While each of the first wall support 62 and the second wall support 64 has been illustrated as a gridded framework, a support defined by a plurality of windows can have any suitable configuration. Selection of a suitable configuration for a support defined by a plurality of windows can be based on various considerations, including the material that forms a main body and/or the desired bone ingrowth intended to be achieved. Examples of configurations considered suitable for a support defined by a plurality of windows includes latticed frameworks, irregular frameworks, gridded frameworks, such that a first wall support has a structural configuration that is the same as, or different than, a structural configuration of a second wall support, and any other configuration considered suitable for a particular embodiment.

In the illustrated embodiment, the first passageway 38 extends from the distal end 16 toward the proximal end 14, through a rear wall 70 defined by the main body 12, and provides access to the interior chamber 34. The rear wall 70 has a thickness 71 that extends from the distal end 16 to the interior chamber 34 and rounded exterior corners that can have any suitable radius of curvature, such as a radius of curvature equal to, greater than, less than, or about 2 millimeters, or between about 1.5 millimeters and about 2.5 millimeters. The thickness 71 can be any suitable thickness, such as a thickness equal to, greater than, less than, or about 2.7 millimeters, or between about 2 millimeters and about 3.5 millimeters. The main body 12 defines a thread 72 within the first passageway 38 that is sized and configured to mate with a fastener, such as a screw. The thread 72 can be any suitable type of thread, such as an M4×0.7 thread, or any other thread considered suitable for a particular embodiment. Optionally, a medical device main body can omit defining a first passageway, such as first passageway 38.

In the illustrated embodiment, the second passageway 40 extends through the upper wall 18 and provides access to the interior chamber 34 and the third passageway 42 extends through the lower wall 20 and provides access to the interior chamber 34. Each of the second passageway 40 and the third passageway 42 has a first radius of curvature 73 at a proximal end of the passageway, a second radius of curvature 75 at a distal end of the passageway, and a length 77 measured along an axis that is parallel to the lengthwise axis 11. The length 77 can be any suitable length, such as a length equal to, greater than, less than, or about 17 millimeters, or between about 12 millimeters and about 23 millimeters.

In the illustrated embodiment, each of the first recess 44 and the second recess 46 extends from the distal end 16 toward the proximal end 14 and has a terminal end 74, rounded corners 76, a length 79, a height 81, and a depth 83. The length 79, the height 81, and the depth 83 can have any suitable dimension. For example, a length 79 can be equal to, greater than, less than, or about 2.1 millimeters, or between about 1.6 millimeters and about 2.6 millimeters, a height 81 can be equal to, greater than, less than, or about 2.8 millimeters, or between about 2.3 millimeters and about 3.3 millimeters, and a depth 83 can be equal to, greater than, less than, or about 2.4 millimeters, or between about 1.9 millimeters and about 2.9 millimeters. The first recess 44 is separated from the second recess 46 by a distance 85 equal to about 5.1 millimeters. However, alternative embodiments can omit the inclusion of a first recess, a second recess, and/or separate a first recess from a second recess any suitable distance, such as distances equal to, greater than, less than, or about 5.1 millimeters, or between about 4.6 millimeters and about 5.7 millimeters. Each of the rounded corners 76 can have a radius of curvature equal to, greater than, less than, or about 0.8 millimeters, or between about 03 millimeters and about 1.3 millimeters.

In the illustrated embodiment, the main body 12 defines a front wall 78, shown best in FIG. 4. The front wall 78 extends from the proximal end 14 to the interior chamber 34 and has a length 87 and a thickness 89. The length 87 and thickness 89 can have any suitable dimensions, such as a length equal to, greater than, less than, or about 2.5 millimeters, or between about 2 millimeters and about 3 millimeters, and a thickness 89 equal to, greater than, less than, or about 1.2 millimeters, or between about 0.7 millimeters and about 1.7 millimeters. In the illustrated embodiment, the portion of the front wall 78 that extends from the proximal end 14 to the plurality of teeth 26 and to the plurality of windows 36 is polished and has a smooth surface to allow for insertion into a space between vertebrae. However, alternative embodiments can omit the inclusion of a polished and/or smoothed surface.

While the main body 12 has been illustrated as having a particular structural arrangement and features have been illustrated as having particular dimensions, a main body can have any suitable structural arrangement and the features of the main body can have any suitable dimensions. Selection of a suitable structural arrangement and of suitable dimensions for the features of a main body can be based on various considerations, including the material that forms a main body and/or the desired bone ingrowth intended to be achieved. For example, a main body can have any suitable length, width at the proximal end, or width at the distal end, such as lengths equal to, greater than, less than, or about 27 millimeters, between about 17 millimeters and about 37 millimeters, or between about 20 millimeters and about 34 millimeters, widths at the proximal end equal to, greater than, less than, or about 3 millimeters, or between about 1 millimeter and 5 millimeters, widths at the distal end equal to, greater than, less than, or about 11 millimeters, or between about 8 millimeters and 14 millimeters, and any other suitable length, width at the proximal end, and/or width at the distal end considered suitable for a particular embodiment.

The medical devices described herein are considered advantageous at least because they provide a device that is capable of an increased bone ingrowth relative to devices that do not include a plurality of windows, a plurality of pockets, a plurality of support elements, a first wall support, and/or a second wall support, as described herein. In addition, the medical devices described herein are considered advantageous at least because they provide a device that has a reduced radiographic signature relative to devices that do not include a plurality of windows, a plurality of pockets, a plurality of support elements, a first wall support, and/or a second wall support, as described herein.

The medical devices described herein can be formed of any suitable material, including presently known and later-developed materials for use in medical devices (e.g., materials considered suitable for implantation in spaces between bones, including within intervertebral spaces). Selection of an appropriate material for a medical device, or each component of a medical device, can be based on various considerations, including the degree to which is desired to visualize the device using visualization techniques and/or equipment subsequent to implantation, the type and/or quantity of bone graft, or other material, that may be used in conjunction with the medical device during treatment, and/or the anatomical features at the location at which the medical device is to be implanted. Examples of materials considered suitable to form a medical device include biocompatible materials, materials that can be made biocompatible, polymers, polyetheretherketone ("PEEK"), metals, stainless steel, titanium, such as TI-6AL-4V ELI (Grade 23) per ASTM F3001, nickel-cobalt-chromium alloys, radiolucent materials, radiopaque materials, combinations of the materials described herein, and any other material considered suitable for a particular embodiment.

The medical devices described herein can be formed using any suitable method or technique of manufacture. Selection of a suitable method or technique can be based on various considerations, such as the type of material that forms a medical device. Examples of methods and techniques considered suitable to form a medical device include conventional forming and/or manufacturing techniques, 3D-printing, fused deposition modeling, stereolithography, digital light processing, selective laser sintering, selective laser melting, electron beam melting, laminated object manufacturing, binder jetting, material jetting, wax casting, additive manufacturing techniques, combinations of the methods and/or techniques described herein, and any other method or technique considered suitable for a particular embodiment. In embodiments in which a medical device is formed (e.g., using 3D-printing or any other method or technique described herein), it is considered advantageous to form the main body from a distal end to a proximal end, from a proximal end to a distal end, and/or from the first passageway to the first lateral wall, the second lateral wall, the upper surface, and the lower surface. By forming the medical device in this manner, the threads defined within a main body passageway can be formed by the manufacturing method or technique, which eliminates the need to tap a passageway subsequent to manufacturing the medical device. In embodiments in which a medical device is formed using 3D-printing techniques (e.g., additive manufacturing) such that a plurality of medical devices is attached to a platform (e.g., scaffolding), it is considered advantageous to remove one or more, or each, of the medical devices by applying a forward and backward force in an alternating manner to the medical device (e.g., rocking the medical device) relative to the platform until it becomes free of the platform. This process eliminates the use of any machines, such as electrical discharge machines, to remove a medical device from a platform. In embodiments in which a medical device is formed using 3D-printing techniques (e.g., additive manufacturing), it is considered advantageous to include a rounded proximal end to avoid any sagging in the material that forms the medical device during manufacture.

FIGS. 10, 11, 12, 13, 14, 15, 16, and 17 illustrate another example implantable medical device 110. The implantable medical device 110 is similar to the implantable medical device 10 illustrated in FIGS. 1, 2, 3, 4, 5, 6, 7, 8, 9, and 9A and described above, except as detailed below. In the illustrated embodiment, the implantable medical device 110 includes a main body 112 that has a lengthwise axis 111, proximal end 114, a distal end 116, a length 113 that extends from the proximal end 114 to the distal end 116, an upper wall 118, a lower wall 120, a first lateral wall 122, a second lateral wall 124, and defines a plurality of teeth 126, a plurality of gullets 128, a plurality of pockets 130, a plurality of support elements 132, an interior chamber 134, a plurality of windows 136, a first passageway 138, a second passageway 140, a third passageway 142, a first recess 144, and a second recess 146.

In the illustrated embodiment, the main body 112 defines a first radius of curvature 202 on the first lateral wall 122 and a second radius of curvature 204 on the second lateral wall 124. In addition, the first lateral wall 122 has a first height 206 and the second lateral wall 124 has a second height 208 that is greater than the first height 206 such that the height of the main body 112 tapers from the second lateral wall 124 to the first lateral wall 122 and each of the upper wall 118 and the lower wall 120 extends from the second lateral wall 124 to the first lateral wall 122 and toward a plane that contains the lengthwise axis 111 of the main body 112 and extends through the first lateral wall 122 and the second lateral wall 124. Each of the upper wall 118 and the lower wall 120 is disposed at an angle 210 relative to a plane that extends from the distal end 116 and is disposed parallel to the lengthwise axis 111. The first radius of curvature 202 and the second radius of curvature 204 can be any suitable radii of curvature. For example, the first radius of curvature 202 can be equal to, greater than, less than, or about 20 millimeters, or between about 15 millimeters and about 25 millimeters, and the second radius of curvature 204 can be equal to, greater than, less than, or about 30 millimeters, or between about 20 millimeters and about 40 millimeters. The angle 210 can be any suitable angle, such as an angle equal to, greater than, less than, or about 6 degrees, or between about 4 degrees and about 8 degrees.

In the illustrated embodiment, the first length 127 of each of the upper wall 118 and the lower wall 120 is equal to about 4.5 millimeters, the third length 131 of each of the upper wall 118 and the lower wall 120 is equal to about 5 millimeters, each of the second width 135 and the third width 137 of the each of the upper wall 118 and the lower wall 120 is equal to about 2.5 millimeters, the rear wall 170 has a thickness 171 equal to about 3.2 millimeters, the proximal end of the second and third passageways 140, 142 has a radius of curvature 212 equal to about 2.5 millimeters, the thread 172 is a M3.5×0.6 thread, and the front wall 178 has a thickness 189 equal to about 1.3 millimeters. However, alternative embodiments can include a main body that has any suitable dimensions.

Various methods of making a medical device are described herein. While the methods described herein are described as a series of acts, it is to be understood and appreciated that the methods are not limited by the order of acts, as some acts may in accordance with these methods, occur in the order shown and/or described, in different orders, and/or concurrently with other acts described herein.

Figure 18:
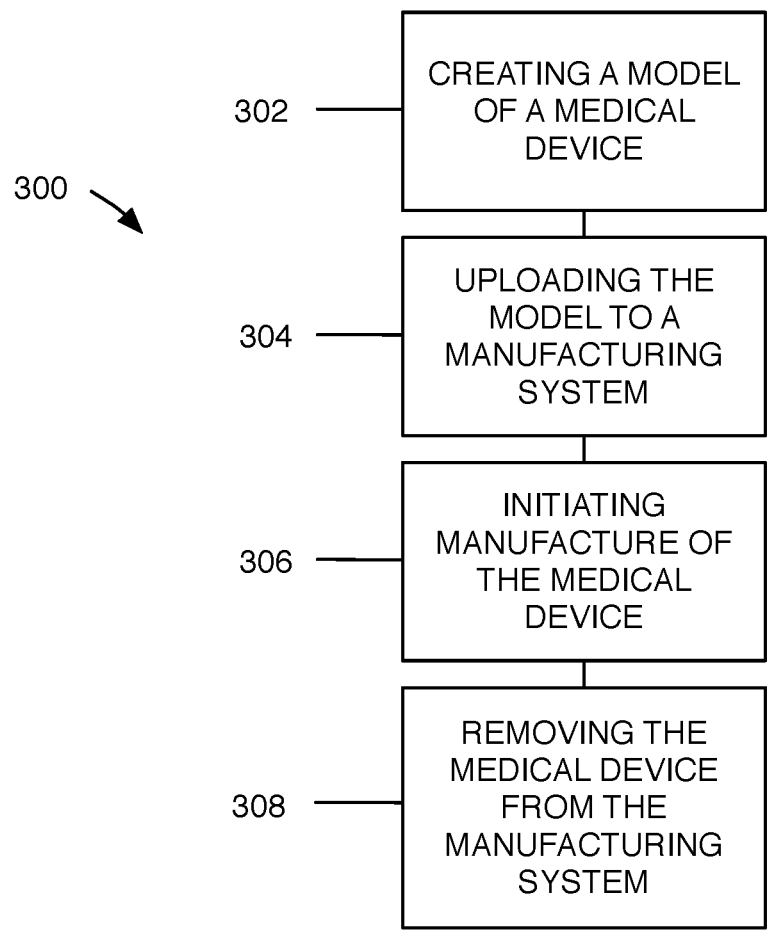
FIG. 18 is a schematic illustration of an example method of making a medical device.

FIG. 18 is a schematic illustration of an example method 300 of making a medical device, such as those described herein.

A first step 302 comprises creating a model of a medical device. Another step 304 comprises uploading the model to a manufacturing system, such as a 3D-printing system. Another step 306 comprises initiating manufacture of the medical device. Another step 308 comprises removing the medical device from the manufacturing system.

Step 302 can be accomplished using any suitable method or technique, such as using computer aided drafting software (e.g., CAD), 3D modeling software, and any suitable method or technique considered suitable for a particular embodiment. This step can comprise creating a model that requires that each pocket of a plurality of pockets be defined in the main body prior to defining a support element within a pocket, or each pocket. This is considered advantageous at least because it delineates the boundaries of each support element included in a medical device. This step can comprise creating a model that requires that the main body be formed from the main body distal end to the main body proximal end and/or from the main body passageway to the upper wall, the lower wall, the first lateral wall, and the second lateral wall (e.g., such that the first passageway threads are created using the manufacturing system). Alternatively, step 302 can comprise creating a model of a plurality of medical devices attached to a platform (e.g., a scaffold) and can be accomplished as described with respect to step 302. Any suitable medical device can be created in step 302, such as implantable medical device 10, implantable medical device 110, medical device 1110, and any other medical device considered suitable for a particular embodiment. Alternatively, step 302 can comprise creating a model of a medical device precursor. Any suitable medical device precursor can be created in this alternative step, such as medical device precursor 510, medical device precursor 710, medical device precursor 910, and any other medical device precursor considered suitable for a particular embodiment.

Step 304 can be accomplished using any suitable method or technique of uploading the model to a manufacturing system, such as using a USB drive, or a network.

Step 306 can be accomplished using any suitable method or technique of initiating the manufacture of the medical device, such as applying an axial force to a start button. This step can comprise manufacturing the medical device, or each medical device of a plurality of medical devices, such that each pocket of a plurality of pockets is formed in the main body prior to forming a support element within a pocket, or each pocket. This is considered advantageous at least because it delineates the boundaries of each support element included in a medical device. This step can comprise manufacturing the medical device, or each medical device of a plurality of medical devices, such that the main body is formed from the main body distal end to the main body proximal end (e.g., the distal end of the medical device main body is formed before the proximal end of the medical device main body) and/or from the main body passageway to the upper wall, the lower wall, the first lateral wall, and the second lateral wall (e.g., such that the first passageway threads are created using the manufacturing system). Alternatively, step 306 can comprise initiating manufacture of the medical device precursor and can be accomplished as described above.

An optional step comprises stopping the manufacture of the medical device, the plurality of medical devices, or the medical device precursor and can be accomplished using any suitable method or technique, such as applying an axial force to a stop button.

Step 308 can be accomplished by applying a force on the medical device and away from the manufacturing system. In embodiments in which a plurality of medical devices is disposed within the manufacturing system and attached to a platform, step 308 comprises removing the plurality of medical devices and the platform from the manufacturing system and can be accomplished by applying a force on a medical device, or multiple medical devices, of the plurality of medical devices and/or on the platform and away from the manufacturing system. Alternatively, step 308 can comprise removing the medical device precursor from the manufacturing system and can be accomplished as described above.

An optional step comprises applying a forward and backward force in an alternating manner to one or more medical devices (e.g., rocking the medical devices) attached to a platform, the platform, and/or to the medical device precursor, along an axis that is parallel to the lengthwise axis of the platform until the one or more medical devices, or the medical device precursor, become free of the platform.

Figure 19:
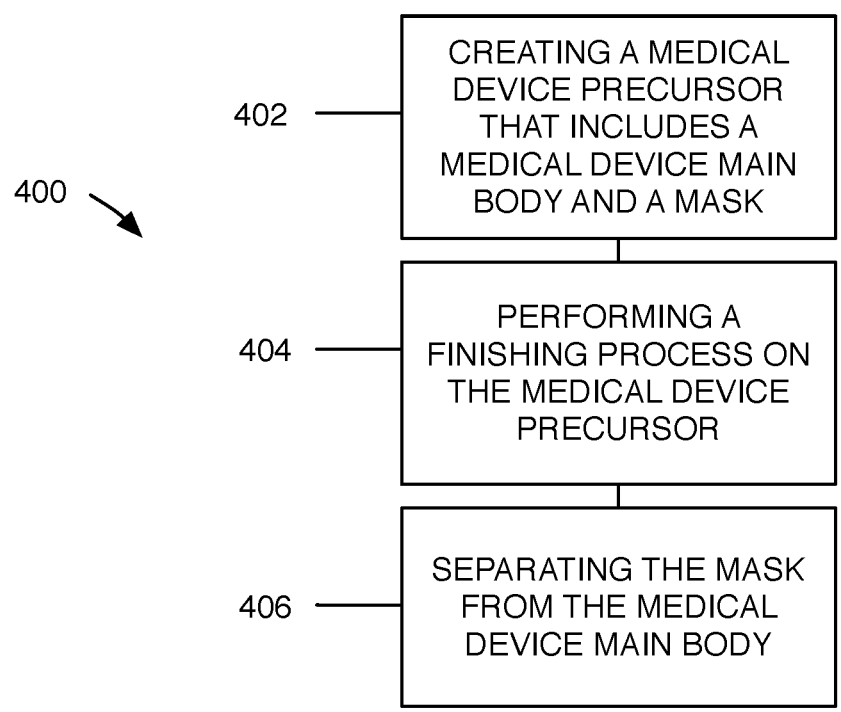
FIG. 19 is a schematic illustration of another example method of making a medical device.

FIG. 19 is a schematic illustration of an example method 400 of making a medical device.

A first step 402 comprises creating a medical device precursor. The medical device precursor includes a medical device main body and a mask attached to (e.g., integrally formed with) the main body. The medical device main body has a first portion exposed to an environment exterior to the medical device main body and a second portion disposed adjacent the mask and shielded from the environment exterior to the medical device main body by the mask. Another step 404 comprises performing a finishing process on the medical device precursor. Another step 406 comprises separating the mask from the medical device main body to produce a medical device.

Figure 20:
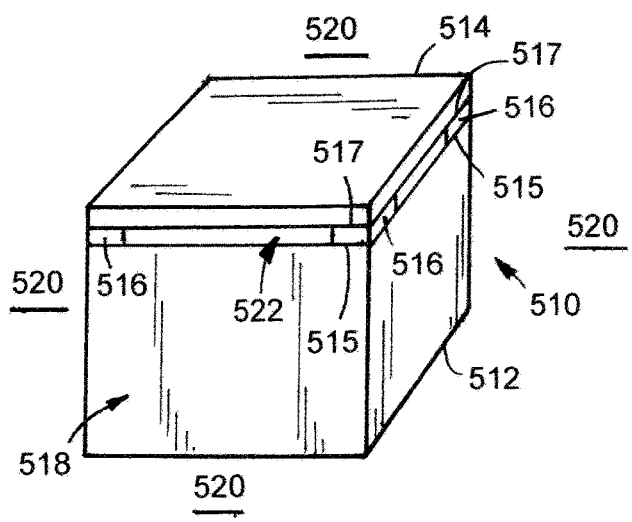
FIG. 20 is a perspective view of an example medical device precursor that includes a medical device main body and a mask.

Step 402 can be accomplished using any suitable method or technique of creating a medical device precursor, such as those described herein. For example, the steps described with respect to method 300 can be utilized to create a medical device precursor. Alternatively, any other method or technique can be utilized to create a medical device precursor, such as 3D-printing techniques (e.g., additive manufacturing). In an alternative embodiment, if a medical device precursor has already been created, step 402 can comprise obtaining a medical device precursor. FIG. 20 illustrates an example medical device precursor 510 that can be created in step 402, or obtained in an alternative embodiment. The medical device precursor 510 has a medical device main body 512 and a mask 514 attached to (e.g., integrally formed with) the medical device main body 512 using a plurality of elongate members 516. Each elongate member of the plurality of elongate members 516 has a first end 515 attached to the medical device main body and a second end 517 attached to the mask 514. The medical device main body 512 has a first portion 518 exposed to an environment 520 exterior to the medical device main body 512 and a second portion 522 disposed adjacent the mask 514 such that the mask shields the second portion 522 from an environment exterior to a medical device main body 512. For example, the mask 514 can be disposed adjacent and cover the second portion 522, disposed adjacent and over the second portion 522, disposed adjacent and contact the second portion 522, disposed adjacent, over, and contacts the second portion 522, disposed adjacent, over, and does not contact the second portion 522, and/or disposed adjacent, over, and separated from the second portion 522 to provide a clearance, such that the mask shields the second portion 522 from an environment exterior to a medical device main body 512. Creating a medical device precursor in this manner is considered advantageous at least because it provides a mechanism for creating a medical device precursor that has an integrally formed, a pre-attached, and/or a pre-defined, mask such that additional processes (e.g., tumbling, blasting, grinding, polishing, shot peening, etching) can be performed on the precursor without requiring the separate attachment of any masks. For example, one or more an integrally formed, pre-defined, and/or pre-attached, masks provide a mechanism for preserving any roughened surface, porous surface, support element (e.g., pocket support, mesh) intended to promote bone ingrowth at the implant and bone interface.

The medical device main body 512 can comprise any suitable medical device main body having any suitable structural arrangement. For example, the illustrated medical device main body can be used as an implantable medical device to fill or otherwise occupy space in a body. Selection of a suitable medical device main body and structural arrangement for a medical device main body can be based on various considerations, including the intended use of a medical device created using method 400. Examples of main bodies considered suitable to utilize in a method of making a medical device include the main bodies described herein, such as main body 12, main body 112, main body 712, main body 912, main body 1112, main bodies that form any suitable medical device, or portion of a medical device, such as implantable medical devices, spacers, intervertebral spacers, screws, nails, plates, stents, frames, knee implants (e.g., tibial stems, femoral cups), total knee implants, shoulder implants (e.g., humeral stem, acetabula cup), total shoulder implants, externally-used medical devices such as external fixation frames, and any other medical device considered suitable for a particular embodiment.

While a single mask 514 has been illustrated as being attached to the medical device main body 512, as having a particular structural arrangement, and as being disposed over only a portion of a medical device main body, any suitable number of masks, having any suitable structural arrangement, formed of any suitable material, can be included in a medical device precursor and can be disposed adjacent to any suitable portion of a medical device, such that the mask covers a portion of a medical device main body (e.g., support element, pocket support), is disposed over a portion of a medical device main body (e.g., support element, pocket support), contacts a portion of a medical device main body (e.g., support element, pocket support), is over and contacts a portion of a medical device main body (e.g., support element, pocket support), is over and does not contact a portion of a medical device main body (e.g., support element, pocket support), and/or is over and separated a portion of a medical device main body (e.g., support element, pocket support) to provide a clearance. Examples of numbers of masks considered suitable to include in a medical device precursor include one, at least one, two, a plurality, three, four, five, more than five, more than ten, and any other number of masks considered suitable for a particular embodiment. Examples of positions considered suitable to locate a mask relative to a medical device main body include those in which a portion, or the entirety, of a medical device main body, or a first surface, a second surface, or a plurality of surfaces of a medical device main body, is disposed adjacent (e.g., over, contacting, over and contacting, over and not contacting, over and separated from to provide a clearance) the mask, contacts the mask or a portion of the mask (e.g., main body, support element, pocket support), is separated from a mask or a portion of a mask (e.g., main body, support element, pocket support), is disposed a distance between about 0.01 millimeters and about 5 millimeters from the mask or a portion of the mask (e.g., main body, support element, pocket support), is disposed a distance between about 0.1 millimeters and about 3 millimeters from the mask or a portion of the mask (e.g., main body, support element, pocket support), is disposed a distance between about 0.01 millimeters and about 1 millimeter from the mask or a portion of the mask (e.g., main body, support element, pocket support), is disposed a distance between about 0.01 millimeters and about 0.3 millimeters from the mask or a portion of the mask (e.g., main body, support element, pocket support), is disposed a distance between about 0.01 millimeters and about 0.2 millimeters from the mask or a portion of the mask (e.g., main body, support element, pocket support), is disposed a distance between about 0.01 millimeters and about 0.1 millimeters from the mask or a portion of the mask (e.g., main body, support element, pocket support), is disposed a distance of about 0.1 millimeters from the mask or a portion of the mask (e.g., main body, support element, pocket support), is disposed a distance that is less than the length, width, or depth of a finishing media, or a portion of a finishing media, and/or any other position considered suitable for a particular embodiment.

While the mask 514 has been illustrated as being attached to the medical device main body 512 using a plurality of elongate members 516, any suitable structure, method, and/or technique can be used to attach a mask to a medical device main body and can be formed of any suitable material. Selection of a suitable structure, method, and/or technique to attach a mask to a medical device main body can be based on various considerations, including the material that forms a mask and/or a medical device main body, or the intended use of the medical device main body. Examples of materials considered suitable to form a mask and/or the structure used to attach a mask to a medical device main body include materials that are presently known and later-developed, biocompatible materials, materials that can be made biocompatible, polymers, PEEK, metals, stainless steel, titanium, such as TI-6AL-4V ELI (Grade 23) per ASTM F3001, nickel-cobalt-chromium alloys, radiolucent materials, radiopaque materials, combinations of the materials described herein, such that the mask if formed of a first material and a medical device main body is formed of a second material that is the same as, or different from, the first material, and any other material considered suitable for a particular embodiment. For example, a mask can be integrally formed with a medical device main body, formed using any suitable method or technique, such as those described herein with respect to forming a medical device or medical device main body, formed as a pattern of material used to shield selected areas of a surface or a portion of a medical device main body, and/or formed of the same material as, or a different material than, the material that forms a medical device main body. In embodiments in which a mask is formed of a material that is different than the material that forms a medical device main body, a precursor can be formed using multiple material additive manufacturing such that the mask is integrally formed with the medical device main body. An example of structure considered suitable to include on an element used to attach a mask to a medical device main body include one or more break points such that the mask can be separated from the medical device main body.

Step 404 can be accomplished by performing any suitable finishing process on the medical device precursor and selection of a finishing process to perform on a medical device precursor can be based on various considerations, including the intended use of the medical device main body and/or the material used to form a medical device main body and/or mask. Examples of finishing processes considered suitable to perform on a medical device precursor include etching, polishing, tumbling, blasting, mechanical blasting, sanding, grinding, polishing, shot peening, any type of mechanical finishing, any type of manual or autonomous finishing, and any other finishing process considered suitable for a particular embodiment. Completing this step using a medical device precursor that includes a medical device main body and an integrally formed, pre-attached, and/or pre-defined, mask is considered advantageous at least because the portions, or the entirety, of the medical device main body disposed adjacent, and masked by, the mask will not be impacted by the finishing process (e.g., the finishing process will not impart any change to the portion of the medical device main body disposed adjacent, and masked by, the mask).

Figure 21:
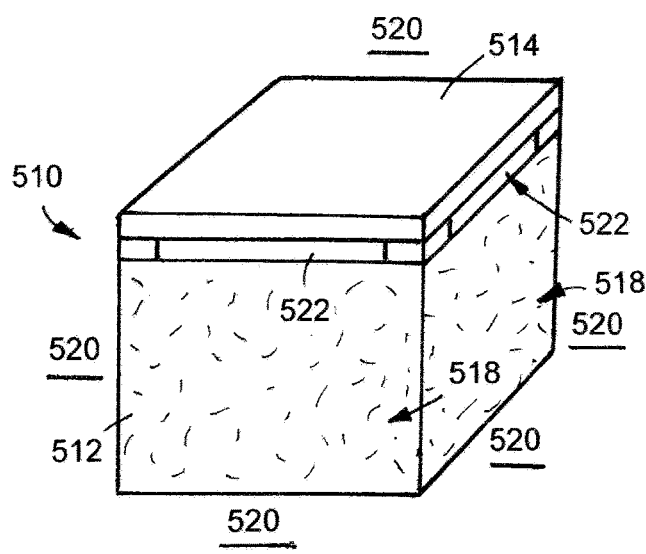
FIG. 21 is a perspective view of the medical device precursor illustrated in FIG. 20 subsequent to the completion of a finishing process.

FIG. 21 illustrates the medical device precursor 510 subsequent to the completion of a finishing process, which in this example included etching the first portion 518 of the medical device main body 512 exposed to an environment 520 exterior to the medical device main body 512. Placement of the mask 514 adjacent the second portion 522 of the medical device main body 512 shielded the second portion 522 from the finishing process resulting in a medical device that has a first portion 518 on which a finishing process has been performed and a second portion 522 which was shielded from the finishing process.

Step 406 can be accomplished using any suitable method or technique of separating a mask from a medical device main body to produce a medical device and selection of a suitable method or technique can be based on various considerations, including the material that forms a mask. This step can optionally be completed subsequent to performing a finishing process on the medical device precursor. Examples of methods and techniques considered suitable to separate a mask from a medical device main body include applying a force (e.g., using a tool, or human hands) on a mask away from and/or toward a medical device main body until the mask becomes free of the medical device main body, applying a force (e.g., using a tool, or human hands) on a mask about an axis that extends through a medical device main body (e.g., parallel or perpendicular to an lengthwise axis) until the mask becomes free of the medical device main body, cutting one or more attachment structures used to attach a mask to a medical device main body using a tool (e.g., knife, rotary tool), grinding a mask, or a portion of a mask (e.g., one or more projection), from a medical device main body, filing a mask, or a portion of a mask (e.g., one or more projection), from a medical device main body, sawing a mask, or a portion of a mask (e.g., one or more projection) from a medical device main body, machining a mask (e.g., CNC machine, manual machining, end mill, cutter, key seat cutter, dovetail cutter, form cutter), or a portion of a mask (e.g., one or more projection), from a medical device main body, separating a mask, or a portion of a mask (e.g., one or more projection), from a medical device main body using an electric discharge machine (EDM) (e.g., wire or die sinking), and any other method or technique considered suitable for a particular embodiment. For example, a rotary tool or a knife can be passed into each slot, or one or more slots, defined by a mask and until it contacts the mask (e.g., projections 818, as described herein) and separates the mask from a medical device main body (e.g., separates each projection of a plurality of projections from a medical device main body). In embodiments in which a knife is used to separate a mask from a medical device main body, any suitable device can be used in combination with the knife to accomplish separation of the mask from the medical device main body. For example, a knife can be attached to an arbor press and used to sheer a mask where it is attached to a medical device main body through each, or one or more, of the slots defined by the mask.

Figure 22:
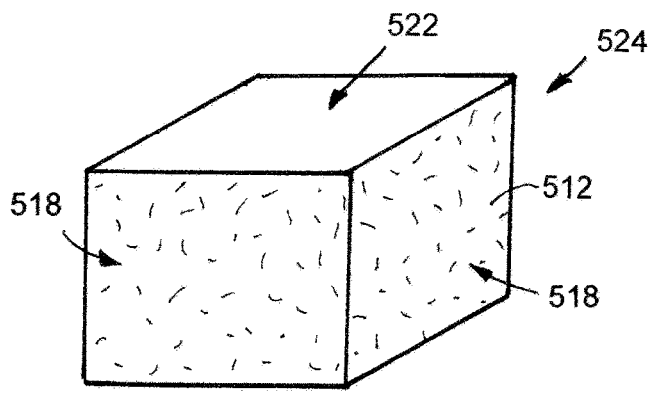
FIG. 22 is a perspective view of the medical device main body illustrated in FIG. 20 subsequent to the separation of the mask from the medical device main body.

FIG. 22 illustrates the medical device main body 512 subsequent to the separation of the mask, resulting in the creation of a medical device 524 that has a first portion 518 on which a finishing process was imparted and a second portion 522 that was masked from the finishing process.

Figure 23:
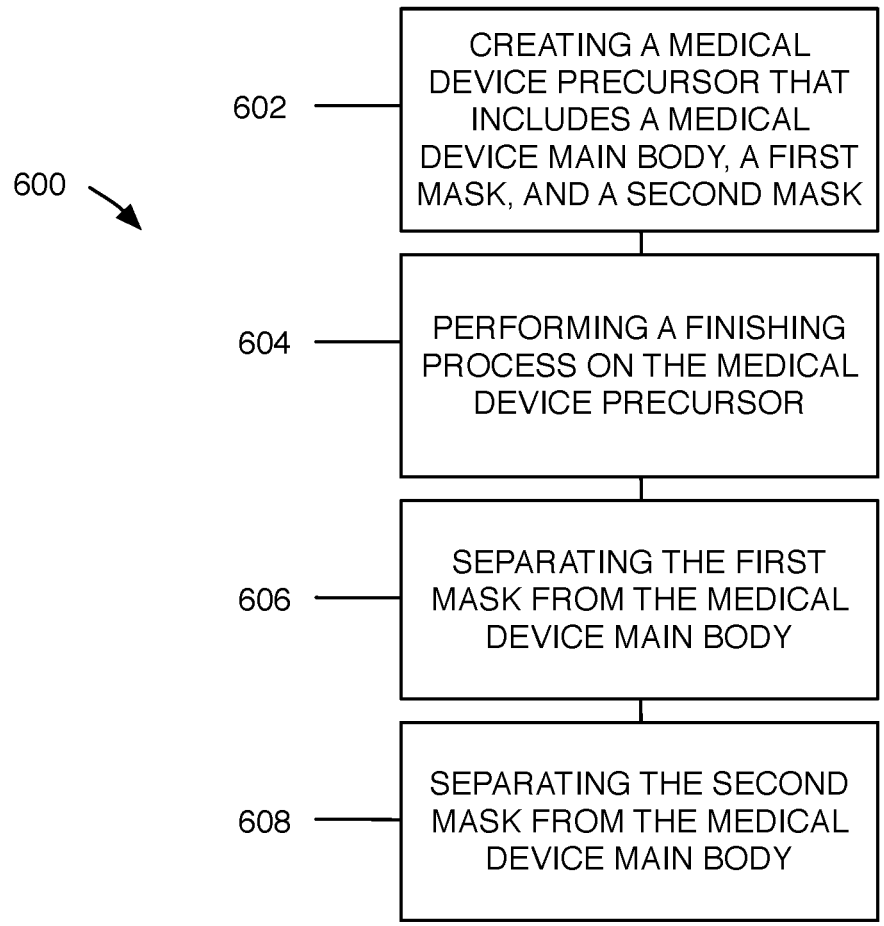
FIG. 23 is a schematic illustration of another example method of making a medical device.
Figure 27:
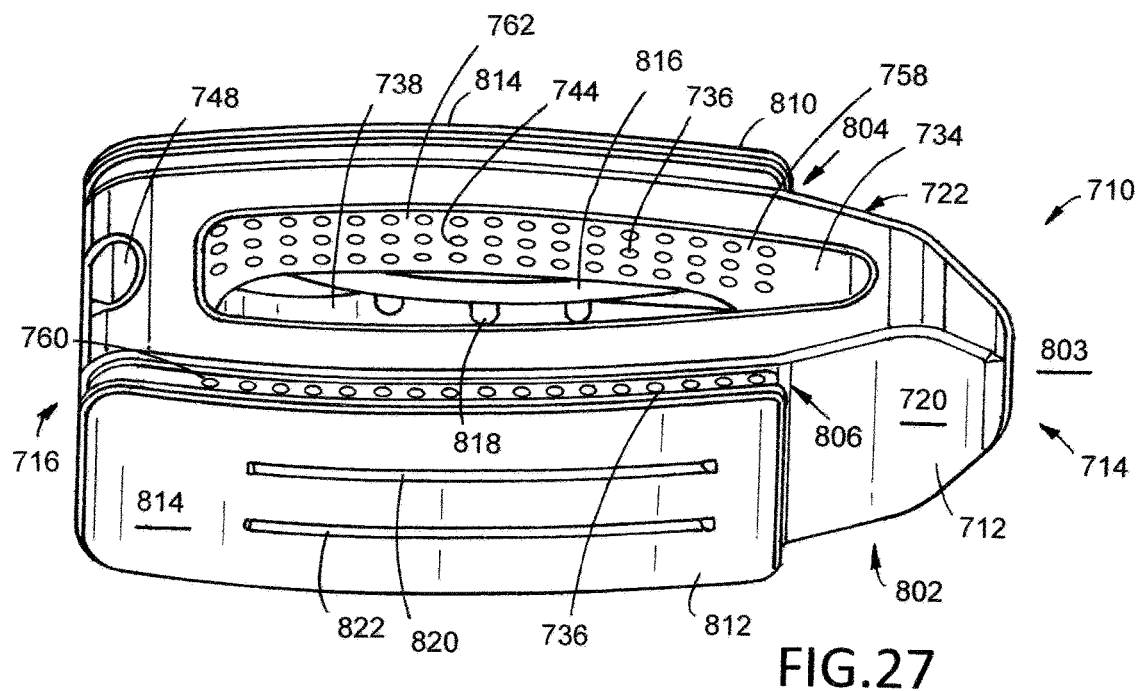
FIG. 27 is another perspective view of the medical device precursor illustrated in FIG. 24.
Figure 28:
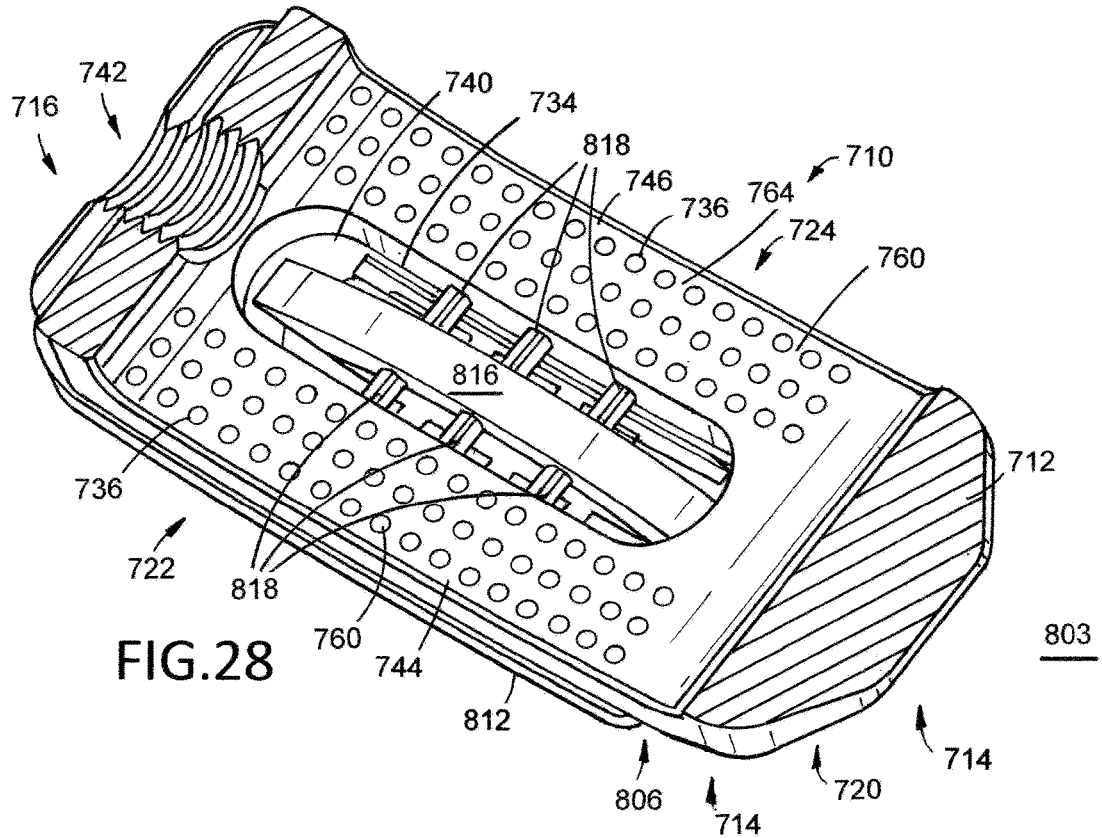
FIG. 28 is a perspective cross-sectional view of the medical device precursor illustrated in FIG. 25 taken along line 28-28.
Figure 31:
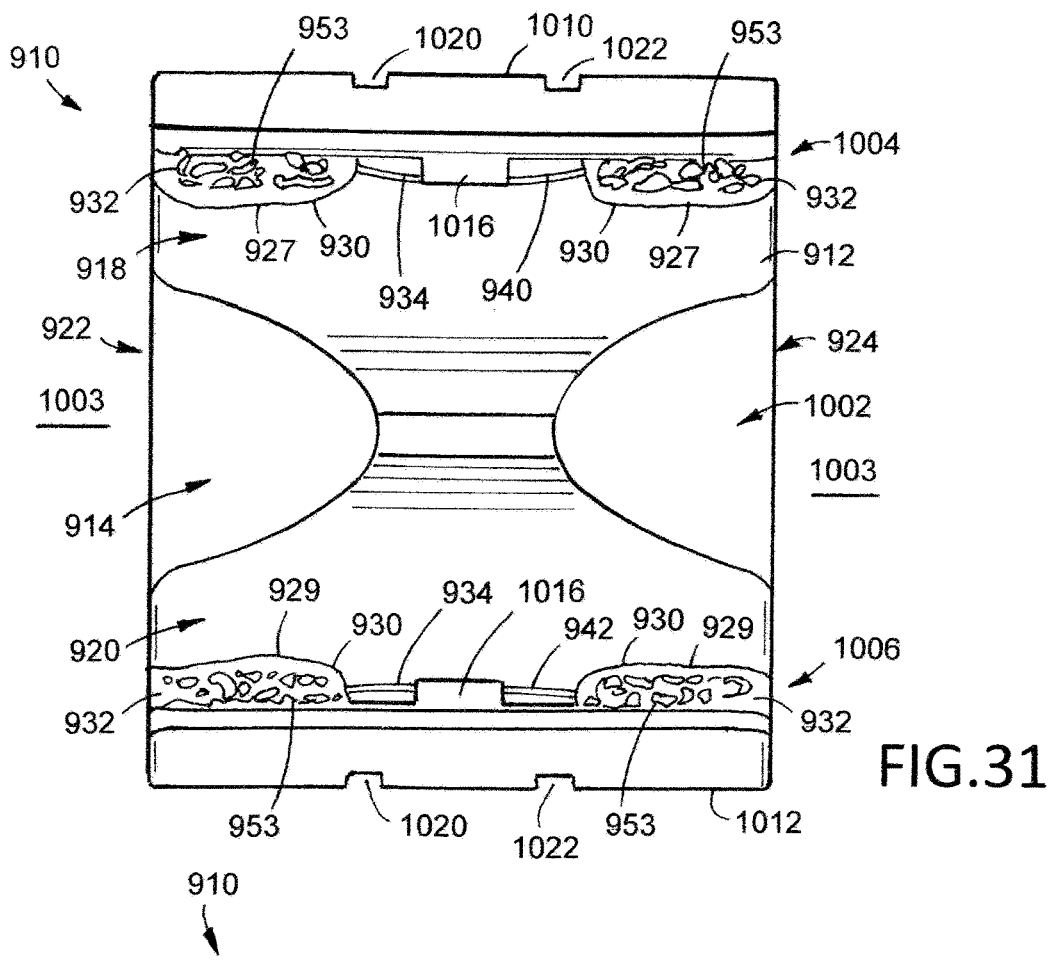
FIG. 31 is a front view of the medical device precursor illustrated in FIG. 29.

FIG. 23 is a schematic illustration of another example method 600 of making a medical device.

A first step 602 comprises creating a medical device precursor. The medical device precursor includes a medical device main body, a first mask integrally formed with the medical device main body, and a second mask integrally formed with the medical device main body. The medical device main body has a first portion exposed to an environment exterior to the medical device main body, a second portion disposed adjacent the first mask and shielded from the environment exterior to the medical device main body by the first mask, and a third portion disposed adjacent the second mask and shielded from the environment exterior to the medical device main body by the second mask. Another step 604 comprises performing a finishing process on the medical device precursor. Another step 606 comprises separating the first mask from the medical device main body. Another step 608 comprises separating the second mask from the medical device main body to produce a medical device.

Step 602 can be accomplished using any suitable method or technique of creating a medical device precursor, such as those described herein. In an alternative embodiment, if a medical device precursor has already been created, step 602 can comprise obtaining a medical device precursor, such as those described herein. FIGS. 24, 25, 26, 27, and 28 illustrate an example medical device precursor 710 that can be created in step 602, or obtained in an alternative embodiment. The medical device precursor 710 has a medical device main body 712, a first mask 810 integrally formed with the medical device main body 712, and a second mask 812 integrally formed with the medical device main body 712. The medical device main body 712 has a first portion 802 exposed to an environment 803 exterior to the medical device main body 712, a second portion 804 disposed adjacent the first mask 810 and shielded from the environment 803 exterior to the medical device main body 712 by the first mask 810, and a third portion 806 disposed adjacent the second mask 812 and shielded from the environment 803 exterior to the medical device main body 712 by the second mask 812. Creating a medical device precursor in this manner is considered advantageous at least because it provides a mechanism for creating a medical device precursor that has an integrally formed, pre-attached, and/or pre-defined, masks such that additional processes (e.g., tumbling, etching) can be performed on the precursor without requiring the separate attachment of any masks.

In the embodiment illustrated in FIGS. 24, 25, 26, 27, and 28, the medical device main body 712 is similar to the implantable medical device main body 12 illustrated in FIGS. 1, 2, 3, 4, 5, 6, 7, 8, 9, and 9A and described above, except as detailed below. However, alternative embodiments can include any suitable medical device main body, such as such as main body 12 (e.g., in which a portion, or the entirety, of the upper wall, the lower wall, the first lateral wall, and/or the second lateral wall are disposed adjacent a mask and shielded from the environment exterior to the medical device main body), main body 112 (e.g., in which a portion, or the entirety, of the upper wall, the lower wall, the first lateral wall, and/or the second lateral wall are disposed adjacent a mask and shielded from the environment exterior to the medical device main body), and/or main bodies that form any suitable medical device, or portion of a medical device.

In the illustrated embodiment, the medical device main body 712 has a lengthwise axis 711, proximal end 714, a distal end 716, a length 713 that extends from the proximal end 714 to the distal end 716, an upper wall 718, a lower wall 720, a first lateral wall 722, a second lateral wall 724, and defines an interior chamber 734, a plurality of windows 736, a first passageway 738, a second passageway 740, a third passageway 742, a fourth passageway 744, a fifth passageway 746, and a first recess 748. While the medical device main body 712 has been illustrated in FIGS. 24, 25, 26, 27, and 28 as being attached to a first mask 810 and a second mask 812, a medical device can include a main body, such as main body 712, without the inclusion of any attached masks such that the main body is provided as a distinct medical device.

The upper wall 718 is disposed adjacent, and covered by, the first mask 810 and shielded from the environment exterior 803 to the medical device main body 712 and the lower wall 720 is disposed adjacent, and covered by, the second mask 812 and shielded from the environment exterior 803 to the medical device main body 712. Each of the first lateral wall 722, the second lateral wall 724, the portion of the upper wall 718 that extends from the proximal end of the first mask 810 to the proximal end 714, the portion of the upper wall 718 that extends from the distal end of the first mask 810 to the distal end 716, the portion of the lower wall 720 that extends from the proximal end of the second mask 812 to the proximal end 714, and the portion of the lower wall 720 that extends from the distal end of the second mask 812 to the distal end 716 is not disposed adjacent, and underneath, a mask and is exposed to the environment exterior 803 to the medical device main body 712 such that one or more finishing processes can be performed on these portions of the medical device main body 712 without imparting the one or more finishing processes on the other portions of the medical device precursor 710.

In the illustrated embodiment, a first set of windows 758 of the plurality of windows 736 extends through the upper wall 718, is disposed adjacent and covered by the first mask 810, and provides access to the interior chamber 734 and a second set of windows 760 of the plurality of windows 736 extends through the lower wall 724, is disposed adjacent and covered by the second mask 812, and provides access to the interior chamber 734. The first set of windows 758 defines a first wall support 762 and the second set of windows 760 defines a second wall support 764. Each of the first wall support 762 and the second wall support 764 is sized and configured to promote bone ingrowth through each window of the plurality of windows 736 and into the interior chamber 734. In the illustrated embodiment, the first wall support 762 is a first gridded framework and the second wall support 764 is a second gridded framework that has the same structural configuration as the first gridded support framework. However, alternative embodiments can include a first gridded framework that is different than a second gridded framework. In the illustrated embodiment, each window of the plurality of windows 736 of the first set of windows 758 is a cylindrical passageway that extends through the upper wall 718 to the interior chamber 734 and each window of the plurality of windows 736 of the second set of windows 760 is a cylindrical passageway that extends through the lower wall 720 to the interior chamber 734.

The fourth passageway 744 extends through the first lateral wall 722 and to the interior chamber 734 and the fifth passageway 746 extends through the second lateral wall 724 and to the interior chamber. The first recess 748 extends from the distal end 716 of the medical device main body 712, toward the proximal end 714 of the medical device main body 712, along the entire length of the distal end 716 of the medical device main body 712, and is in communication with the third passageway 742.

While various portions of the medical device main body 712 have been illustrated as being exposed to an environment exterior to the medical device main body, any suitable portion, or the entirety, of a medical device main body can be exposed, or shielded, from an environment exterior to the medical device main body. For example, a portion of, or the entirety of, an upper wall, a lower wall, a first lateral wall, a second lateral wall, a plurality of teeth, a plurality of gullets, a plurality of pockets, a plurality of support elements (e.g., pocket supports, mesh), an interior chamber, a plurality of windows, a first passageway, a second passageway, a third passageway, a fourth passageway, a fifth passageway, a first recess, a second recess, and/or any other portion of a medical device main body can be disposed adjacent a mask, such that the mask covers a portion of the main body (e.g., support element, pocket supports), is disposed over a portion of the main body (e.g., support element, pocket supports), contacts a portion of the main body (e.g., support element, pocket supports), is over and contacts a portion of the main body (e.g., support element, pocket supports), is over and does not contact a portion of the main body (e.g., support element, pocket supports), and/or is over and separated from a portion of the main body (e.g., support element, pocket supports) to provide a clearance, such that the mask shields the main body, or portion of the main body, from an environment exterior to a medical device main body or exposed to an environment exterior to a medical device main body.

Each of the first mask 810 and the second mask 812 is integrally formed with the medical device main body 712 and has a main body 814, an elongate member 816, and a plurality of projections 818. The main body 814 defines a first slot 820 and a second slot 822 that extends through the main body 814 and provides access between an environment 803 exterior to the medical device main body 712 and the interior chamber 734. The elongate member 816 of the first mask 810 extends from the main body 814, through the first passageway 738, and into the interior chamber 734. The elongate member 816 of the second mask 812 extends from the main body 814, through the second passageway 740, and into the interior chamber 734. Each projection of the plurality of projections 818 extends from the elongate member 816 and is attached to the medical device main body 712. As shown in FIG. 26, each projection of the plurality of projections 818 is disposed on a plane that extends through a slot 820, 822 defined by the main body 814. This arrangement is considered advantageous at least because it allows for a portion of a tool, such as a rotary tool, to be passed into a slot 820, 822 and used to separate (e.g., cut) each projection of the plurality of projections 818 from the medical device main body 712 such that the masks 810, 812 become free from the medical device main body 712.

While each of the masks 810, 812 has been illustrated as including a first slot 820 and a second slot 822, a mask can include any suitable structural arrangement that provides a mechanism for shielding a portion of a medical device main body and allowing for the mask to be separated from the medical device main body subsequent to any finishing processes being performed on a portion of the medical device main body. Examples of suitable structural arrangements considered suitable for a mask include those that define one or more slots, one or more passageways, those that are elongated, cuboidal, cylindrical, and any other structural arrangement considered suitable for a particular embodiment.

FIGS. 29, 30, 31, and 32 illustrate another example medical device precursor 910 that can be created in step 602, or obtained in an alternative embodiment. The medical device precursor 910 has a medical device main body 912, a first mask 1010 integrally formed with the medical device main body 912, and a second mask 1012 integrally formed with the medical device main body 912. The medical device main body 912 has a first portion 1002 exposed to an environment 1003 exterior to the medical device main body 912, a second portion 1004 disposed adjacent the first mask 1010 and shielded from the environment 1003 exterior to the medical device main body 912 by the first mask 1010, and a third portion 1006 disposed adjacent the second mask 1012 and shielded from the environment 1003 exterior to the medical device main body 912 by the second mask 1012.

In the embodiment illustrated in FIGS. 29, 30, 31, and 32, the medical device main body 912 is similar to the implantable medical device main body 12 illustrated in FIGS. 1, 2, 3, 4, 5, 6, 7, 8, 9, and 9A and described above, except as detailed below. In addition, in the embodiment illustrated in FIGS. 29, 30, 31, and 32, the first mask 1010 and the second mask 1012 are similar to the first mask 810 and second mask 812 illustrated in FIGS. 24, 25, 26, 27, and 28 and described above, except as detailed below In the illustrated embodiment, the medical device main body 912 has a lengthwise axis 911, proximal end 914, a distal end 916, an upper wall 918, a lower wall 920, a first lateral wall 922, a second lateral wall 924, and defines a plurality of pockets 930, a plurality of support elements 932, an interior chamber 934, a plurality of windows 936, a first passageway 938, a second passageway 940, a third passageway 942, and a first recess 944. While the medical device main body 912 has been illustrated in FIGS. 29, 30, 31, and 32 as being attached to a first mask 1010 and a second mask 1012, a medical device can include a main body, such as main body 912, without the inclusion of any attached masks such that the main body is provided as a distinct medical device.

In the illustrated embodiment, a first pocket 927 of the plurality of pockets 930 extends into the main body 912 on the upper wall 918 and a second pocket 929 of the plurality of pockets 930 extends into the main body 912 on the lower wall 920. Each of the first pocket 927 and the second pocket 929 has a U-shaped configuration and extends between the proximal end 914 and the distal end 916 of the main body 912. However, alternative embodiments can include a pocket that has any suitable configuration, such as a U-shaped configuration that has gaps in the pocket to form a portion of an upper surface and/or a lower surface. Each pocket of the plurality of pockets 930 is sized and configured to receive a support element of the plurality of support elements 932. A support element of the plurality of support elements 932 is disposed within each pocket of the plurality of pockets 930 and is sized and configured to promote bone ingrowth. In the illustrated embodiment, each support element of the plurality of support elements 932 is formed of, and comprises, a semi-porous trabecular-like mesh 953 that allows for an increased bone ingrowth relative to devices that do not include a plurality of support elements 932. The support elements 932 disposed within the first pocket 927 are disposed adjacent (e.g., covered by) the first mask 1010 and the support elements 932 disposed within the second pocket 929 are disposed adjacent (e.g., covered by) the second mask 1012.

Figure 32:
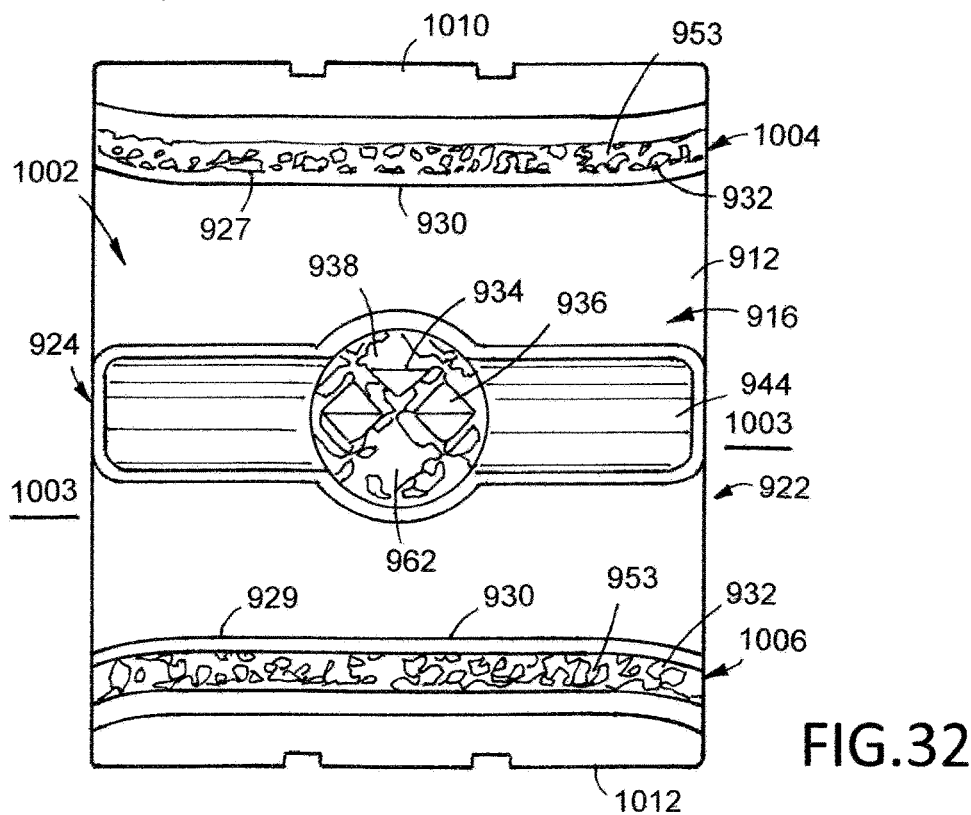
FIG. 32 is a rear view of the medical device precursor illustrated in FIG. 29.
Figure 35:
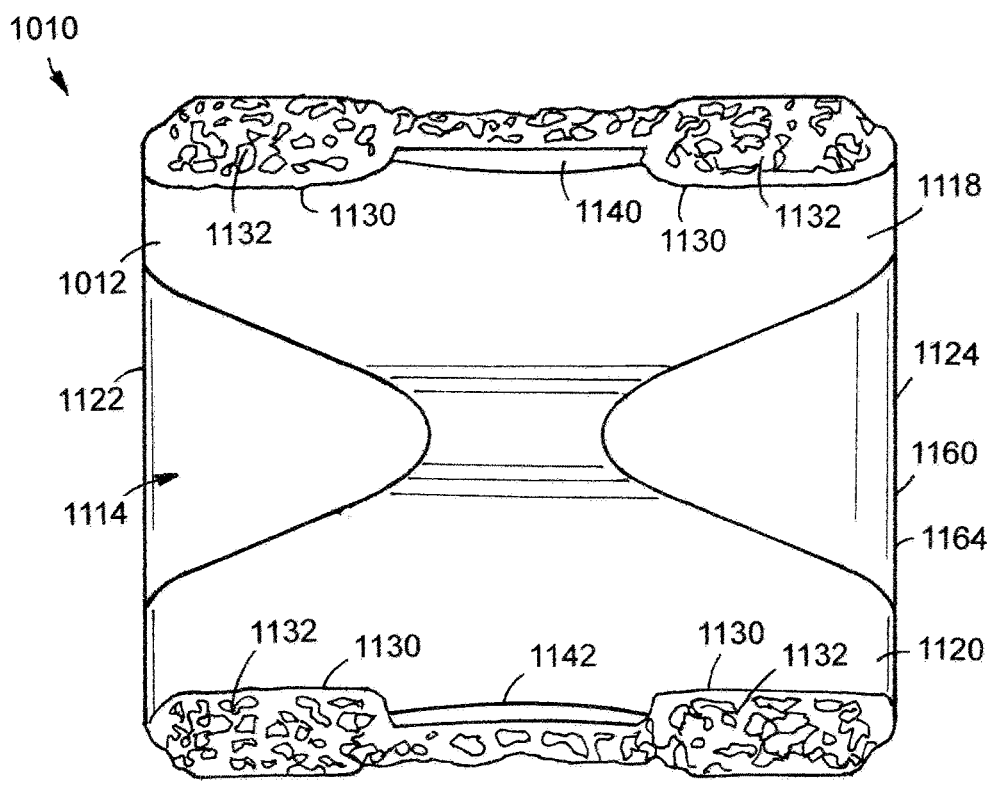
FIG. 35 is a front view of the medical device illustrated in FIG. 33.

In the illustrated embodiment, the plurality of windows 936 extends through the first lateral wall 922, into the interior chamber 934, as shown in FIG. 32, and through the second lateral wall 924. The plurality of windows 936 is defined throughout the entirety of the interior chamber 934 and defines a first wall support 962 (e.g., first gridded framework) which is different than the plurality of support elements 932. Alternative embodiments, however, can include a plurality of windows that is only defined throughout a portion of an interior chamber.

The first recess 944 extends from the distal end 916 of the medical device main body 912, toward the proximal end 914 of the medical device main body 912, along the entire length of the distal end 916 of the medical device main body 912, and is in communication with the third passageway 942.

The upper wall 918 is disposed adjacent, and underneath, the first mask 1010 and shielded from the environment exterior 1003 to the medical device main body 912 and the lower wall 920 is disposed adjacent, and underneath, the second mask 1012 and shielded from the environment exterior 1003 to the medical device main body 912. This results in the plurality of pockets 730 and the plurality of support elements 732 being disposed adjacent, and underneath, a mask 1010, 1012 and shielded from the environment exterior 1003 to the medical device main body 912. Each of the first lateral wall 922, the second lateral wall 924, the portion of the upper wall 918 that extends from the proximal end of the first mask 1010 to the proximal end 914, the portion of the upper wall 918 that extends from the distal end of the first mask 1010 to the distal end 916, the portion of the lower wall 920 that extends from the proximal end of the second mask 1012 to the proximal end 914, and the portion of the lower wall 920 that extends from the distal end of the second mask 1012 to the distal end 916 is not disposed adjacent, and underneath, a mask and is exposed to the environment exterior 1003 to the medical device main body 912 such that one or more finishing processes can be performed on these portions of the medical device main body 912 without imparting the one or more finishing processes on the other portions of the medical device precursor 910.

Each of the first mask 1010 and the second mask 1012 integrally formed with to the medical device main body 912 and has a main body 1014, an elongate member 1016, and a plurality of projections 1018. Alternative embodiments, however, can include a first mask and/or a second mask that is attached to, or releasably attached to, a medical device main body. The main body 1014 defines a first slot 1020 and a second slot 1022 that extends through the main body 1014 and provides access between an environment 1003 exterior to the medical device main body 912 and the interior chamber 934. The elongate member 1016 of the first mask 1010 extends from the main body 1014, through the first passageway 938, and into the interior chamber 934. The elongate member 1016 of the second mask 1012 extends from the main body 1014, through the second passageway 940, and into the interior chamber 934. Each projection of the plurality of projections 1018 extends from the elongate member 1016 and is attached to the medical device main body 912. As shown in FIG. 29, each projection of the plurality of projections 1018 is disposed on a plane that extends through a slot 1020, 1022 defined by the main body 1014.

Step 604 can be accomplished by performing any suitable finishing process on the medical device precursor, such as those described with respect to step 404.

Step 606 can be accomplished using any suitable method or technique of separating a mask from a medical device main body, such as those described with respect to step 406. This step can optionally be completed subsequent to performing a finishing process on the medical device precursor. In embodiments in which a mask is being separated from medical device precursor 710, step 606 can be accomplished by passing a rotary tool into slots 820, 822 of the first mask 810 and cutting each projection of the plurality of projections 818 such that the mask 810 becomes free from the medical device main body 712. In embodiments in which a mask is being separated from medical device precursor 910, step 606 can be accomplished by passing a knife, or other tool, into slots 1020, 1022 of the first mask 1010 and cutting each projection of the plurality of projections 1018 such that the mask 1010 becomes free from the medical device main body 912.

Step 608 can be accomplished using any suitable method or technique of separating a mask from a medical device main body to produce a medical device. This step can optionally be completed subsequent to performing a finishing process on the medical device precursor. In embodiments in which a mask is being separated from medical device precursor 710, step 608 can be accomplished by passing a rotary tool into slots 820, 822 of the second mask 812 and cutting each projection of the plurality of projections 818 such that the mask 812 becomes free from the medical device main body 712. In embodiments in which a mask is being separated from medical device precursor 910, step 606 can be accomplished by passing a knife, or other tool, into slots 1020, 1022 of the second mask 1012 and cutting each projection of the plurality of projections 1018 such that the mask 1012 becomes free from the medical device main body 912.

FIGS. 33, 34, 35, and 36 illustrate an example medical device 1110 subsequent to the separation of a first mask and a second mask. The medical device 1110 has a medical device main body 1112 that is similar to the medical device main body 912 illustrated in FIGS. 29, 30, 31, and 32 and described above, except as detailed below.

Figure 36:
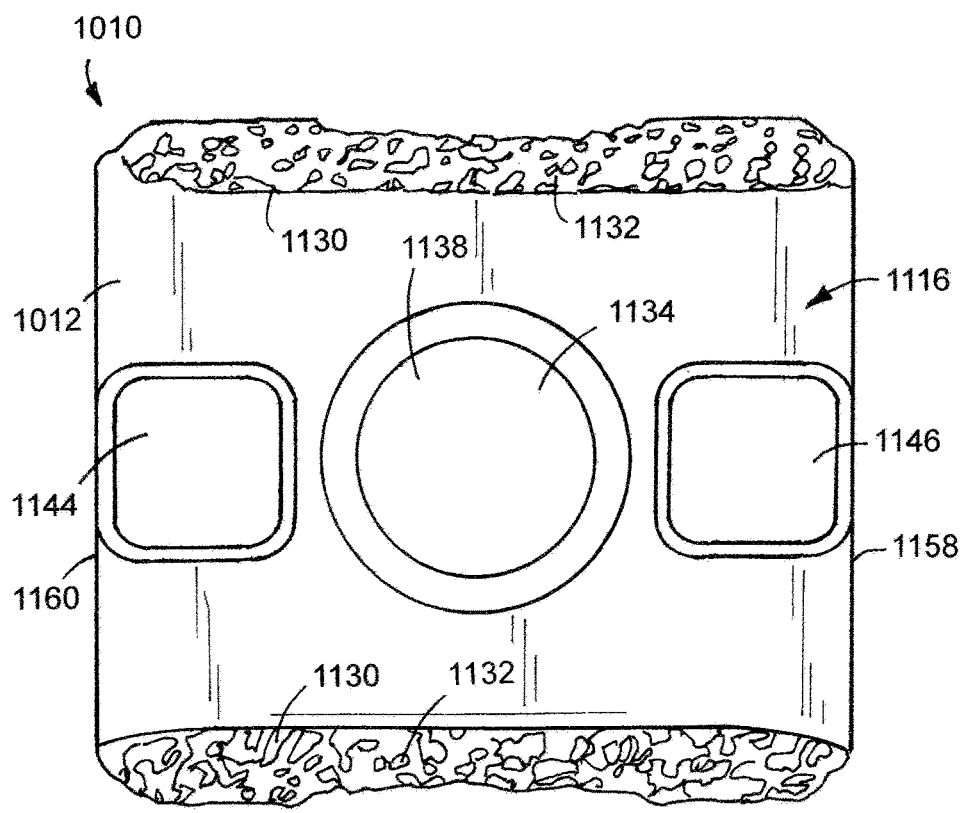
FIG. 36 is a rear view of the medical device illustrated in FIG. 33.

In the illustrated embodiment, the medical device main body 1112 has a lengthwise axis 1111, proximal end 1114, a distal end 1116, an upper wall 1118, a lower wall 1120, a first lateral wall 1122, a second lateral wall 1124, and defines a plurality of pockets 1130, a plurality of support elements 1132, an interior chamber 1134, a plurality of windows 1136, a first passageway 1138, a second passageway 1140, a third passageway 1142, a first recess 1144, and a second recess 1146. Each of the first recess 1144 and the second recess 1146 extends from the distal end 1116 toward the proximal end 1114, as shown in FIG. 36.

In the illustrated embodiment, a first set of windows 1158 of the plurality of windows 1136 extends through the first lateral wall 1122 and provides access to the interior chamber 1134, a second set of windows 1160 of the plurality of windows 1136 extends through the second lateral wall 1124 and provides access to the interior chamber 1134, a third set of windows 1159 of the plurality of windows 1136 extends through the upper wall 1118 and provides access to the interior chamber 1134, and a fourth set of windows 1161 of the plurality of windows 1136 extends through the lower wall 1124 and provides access to the interior chamber 1134. The first set of windows 1158 defines a first wall support 1162, the second set of windows 1160 defines a second wall support 1164, the third set of windows 1159 defines a third wall support 1163, and the fourth set of windows 1161 defines a fourth wall support 1165. Each of the first wall support 1162, the second wall support 1164, the third wall support 1163, and the fourth wall support 1165 is different than the plurality of support elements 1132 and is sized and configured to promote bone ingrowth. In the illustrated embodiment, the first wall support 1162 is a first gridded framework, the second wall support 1164 is a second gridded framework, the third wall support 1163 is a third gridded framework, and the fourth wall support 1165 is a fourth gridded framework. The first gridded framework is the same as the second gridded framework. The third gridded framework is the same as the fourth gridded framework. In the illustrated embodiment, each window of the plurality of windows 1136 of the first set of windows 1158 and the second set of windows 1160 is a is a rectangular prism, each window of the plurality of windows 1136 of the third set of windows 1159 is a cylindrical passageway that extends through the upper wall 1118 to the interior chamber 1134, and each window of the plurality of windows 1136 of the fourth set of windows 1161 is a cylindrical passageway that extends through the lower wall 1120 to the interior chamber 1134.

In the illustrated embodiment, the upper wall 1118 was disposed adjacent, and underneath, a first mask and shielded from an environment exterior to the medical device main body 1112 and the lower wall 1120 was disposed adjacent, and underneath, a second mask and shielded from an environment exterior to the medical device main body 1112. As a result, the plurality of pockets 1130 and the plurality of support elements 1132 were disposed adjacent, and underneath, a mask and shielded from an environment exterior to the medical device main body 1112 such that no finishing process was imparted on these portions of the medical device main body 1112. A medical device manufactured in this manner is considered advantageous at least because it results in a medical device that is partially subjected to a finishing process and allows for portions of the medical device main body to be shielded from one or more finishing processes. For example, by shielding the plurality of pockets 1130 and the plurality of support elements 1132 from a finishing process, the structural arrangement of the plurality of pockets 1130 and the plurality of support elements 1132 can remain unchanged subsequent to creation to increase bone ingrowth and prevent any voids created by the plurality of pockets 1130 and/or the plurality of support elements 1132 from being filled or otherwise changed by the finishing process.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A method of making a medical device, the method comprising:
   creating a medical device precursor, the medical device precursor including:
      a medical device main body having a proximal end, a distal end, an upper wall, a lower wall, a first lateral wall, a second lateral wall, and defining a pocket extending into the medical device main body, a support element disposed within the pocket, and an interior chamber; and
      a first mask integrally formed with the medical device main body, the first mask having a first mask main body disposed adjacent the support element;
   performing a finishing process on the medical device precursor; and
   separating the first mask from the medical device main body subsequent to performing the finishing process on the medical device precursor to produce said medical device;
   wherein the first mask comprises an elongate member and a plurality of projections, the first mask main body defining a slot, the elongate member extending from the first mask main body and into the interior chamber, each projection of the plurality of projections extending from the elongate member and attached to the medical device main body; and
   wherein separating the first mask from the medical device main body comprises passing a tool into the slot to separate each projection of the plurality of projections from the medical device main body.

2. The method of claim 1, wherein the first mask main body contacts the support element.

3. The method of claim 1, wherein the first mask main body is separated from the support element a distance of about 0.1 millimeters.

4. The method of claim 1, wherein the first mask is formed of a first material and the medical device main body is formed of a second material.

5. The method of claim 4, wherein the first material is the same as the second material.

6. The method of claim 4, wherein the first material is different than the second material.

7. The method of claim 1, wherein the finishing process comprises polishing.

8. The method of claim 1, wherein creating a medical device precursor comprises creating a medical device precursor using additive manufacturing.

9. The method of claim 1, wherein the medical device main body has a plurality of windows, a first set of windows of the plurality of windows extending through the first lateral wall and providing access to the interior chamber, a second set of windows of the plurality of windows extending through the second lateral wall and providing access to the interior chamber, the first set of windows defining a first wall support and the second set of windows defining a second wall support, each of the first wall support and the second wall support is different than the support element.

10. The method of claim 9, wherein the first wall support comprises a first gridded framework and the second wall support comprises a second gridded framework that is the same as the first gridded framework.

11. The method of claim 9, wherein a third set of windows of the plurality of windows extends through the upper wall and provides access to the interior chamber, the third set of windows of the plurality of windows defines a third wall support that is different than the first wall support.

12. The method of claim 1, wherein the support element comprises a mesh.

13. The method of claim 1, wherein the medical device main body is formed of titanium.

14. The method of claim 1, wherein the medical device main body defines a plurality of teeth, a first set of teeth of the plurality of teeth extending from the upper wall and away from the lower wall, a second set of teeth of the plurality of teeth extending from the lower wall and away from the upper wall;
   wherein the medical device main body defines a plurality of pockets, a pocket of the plurality of pockets extending into the medical device main body on each tooth of the plurality of teeth;
   wherein the medical device main body defines a plurality of support elements, a support element of the plurality of support elements disposed within each pocket of the plurality of pockets; and
   wherein the first mask main body is disposed adjacent each support element of the plurality of support elements.

15. The method of claim 1, wherein the medical device main body defines a plurality of pockets, a first pocket of the plurality of pockets extending into the medical device main body on the upper wall, and a second pocket of the plurality of pockets extending into the medical device main body on the lower wall; and
   wherein the medical device main body defines a plurality of support elements, a support element of the plurality of support elements disposed within each pocket of the plurality of pockets.

16. The method of claim 15, wherein the first mask main body is disposed adjacent the first pocket; and
   wherein the medical device precursor includes a second mask integrally formed with the medical device main body, the second mask having a second mask main body disposed adjacent the second pocket;
   further comprising separating the second mask from the medical device main body subsequent to performing a finishing process on the medical device precursor to produce said medical device.

* * * * *